(12) United States Patent
Schaser et al.

(10) Patent No.: US 12,286,639 B2
(45) Date of Patent: Apr. 29, 2025

(54) LDLR NEGATIVE PACKAGING CELL LINE FOR THE PRODUCTION OF VSV-G PSEUDOTYPED RETROVIRAL VECTOR PARTICLES OR VIRUS PARTICLES THEREOF

(71) Applicant: Miltenyi Biotec B.V. & Co. KG, Bergisch Gladbach (DE)

(72) Inventors: Thomas Schaser, Rösrath (DE); Johann-Christoph Dettmann, Bergisch Gladbach (DE); Martin Meyer, Kürten (DE); Ian Johnston, Rösrath (DE)

(73) Assignee: MILTENYI BIOTEC B.V. & CO. KG, Bergisch Gladbach (DE)

( * ) Notice: Subject to any disclaimer, the term of this patent is extended or adjusted under 35 U.S.C. 154(b) by 1093 days.

(21) Appl. No.: 17/264,763

(22) PCT Filed: Aug. 28, 2019

(86) PCT No.: PCT/EP2019/072931
§ 371 (c)(1),
(2) Date: Jan. 29, 2021

(87) PCT Pub. No.: WO2020/043765
PCT Pub. Date: Mar. 5, 2020

(65) Prior Publication Data
US 2021/0301307 A1  Sep. 30, 2021

(30) Foreign Application Priority Data

Aug. 30, 2018  (EP) .................................... 18191784

(51) Int. Cl.
*C12N 15/86* (2006.01)
*C12N 7/00* (2006.01)

(52) U.S. Cl.
CPC ............... *C12N 15/86* (2013.01); *C12N 7/00* (2013.01); *C12N 2740/15023* (2013.01); *C12N 2740/15043* (2013.01); *C12N 2740/15052* (2013.01); *C12N 2810/6081* (2013.01)

(58) Field of Classification Search
None
See application file for complete search history.

(56) References Cited

FOREIGN PATENT DOCUMENTS

| JP | 2011092025 A | 5/2011 |
| WO | 2020043765 A1 | 3/2020 |

OTHER PUBLICATIONS

Otahal A, Fuchs R, Al-Allaf FA, Blaas D. Release of Vesicular Stomatitis Virus Spike Protein G-Pseudotyped Lentivirus from the Host Cell Is Impaired upon Low-Density Lipoprotein Receptor Overexpression. J Virol. Nov. 2015;89(22):11723-6. doi: 10.1128/JVI.01869-15. Epub Sep. 2, 2015. (Year: 2015).*
Merten OW, Hebben M, Bovolenta C. Production of lentiviral vectors. Mol Ther Methods Clin Dev. Apr. 13, 2016;3:16017. doi: 10.1038/mtm.2016.17. PMID: 27110581; PMCID: PMC4830361. (Year: 2016).*
Otahal A, Fuchs R, Al-Allaf FA, Blaas D. Release of Vesicular Stomatitis Virus Spike Protein G-Pseudotyped Lentivirus from the Host Cell Is Impaired upon Low-Density Lipoprotein Receptor Overexpression. J Virol. Nov. 2015;89(22):11723-6. (Year: 2015).*
Cockrell AS, Ma H, Fu K, Mccown TJ, Kafri T. A trans-lentiviral packaging cell line for high-titer conditional self-inactivating HIV-1 vectors. Mol Ther. Aug. 2006;14(2):276-84. doi: 10.1016/j.ymthe. 2005.12.015. Epub Mar. 3, 2006. PMID: 16516556. (Year: 2006).*
Tareen SU, Nicolai CJ, Campbell DJ, Flynn PA, Slough MM, Vin CD, Kelley-Clarke B, Odegard JM, Robbins SH. A Rev-Independent gag/pol Eliminates Detectable psi-gag Recombination in Lentiviral Vectors. Biores Open Access. Dec. 1, 2013;2(6):421-30. (Year: 2013).*
Ramezani A, Hawley RG. Overview of the HIV-1 Lentiviral Vector System. Curr Protoc Mol Biol. Nov. 2002;Chapter 16:Unit 16.21. doi: 10.1002/0471142727.mb1621s60. PMID: 18265302. (Year: 2002).*
Wang et al., "Functional Characterization of Two Low-Density Lipoprotein Receptor Gene Mutations in Two Chinese Patients with Familial Hypercholesterolemia", PLoS ONE 9 (3), e92703, Published Mar. 26, 2024, 10 pages.
Amirache et al., Mystery Solved: VSV-G-LVs Do Not Allow Efficient Gene Transfer into Unstimulated T Cells, B Cells, and HSCs Because They Lack the LDL Receptor, Blood, vol. 123, No. 9, Feb. 2014, pp. 1422-1424.
Cronin et al., Altering the Tropism of Lentiviral Vectors Through Pseudotyping, Current Gene Therapy, vol. 5, No. 4, Aug. 1, 2005, pp. 1-19.
Finkelshtein et al., LDL Receptor and Its Family Members Serve as the Cellular Receptors for Vesicular Stomatitis Virus, Procedeedings of the National Academy of Sciences, vol. 110, N. 8, Apr. 30, 2013, pp. 7306-7311.
Guyader et al., Role for Human Immunodeficiency Virus Type 1 Membrane Cholesterol in Viral Internalization, Journal of Virology, vol. 76, No. 20, Oct. 2002, pp. 10356-10364.
Merten et al., Manufacturing of Viral Vectors for Gene Therapy: Part I. Upstream Processing, Pharmaceutical Bioprocessing, vol. 2, No. 2, Apr. 2014, pp. 183-203.
Nikolic et al., Structural Basis for the Recognition of LDL-receptor Family Members by VSV Glycoprotein, Nature Communications, vol. 9, No. 1029, Mar. 12, 2018, pp. 1-12.
Otahal et al., Release of VSV-G spike protein . . . J. Virol. Nov. 2015;89(22):11723-6.

(Continued)

*Primary Examiner* — Allison M Fox
*Assistant Examiner* — Qinhua Gu
(74) *Attorney, Agent, or Firm* — Kilpatrick Townsend & Stockton LLP

(57) ABSTRACT

The present invention provides the use of a packaging cell line for the production of VSV-G pseudotyped retroviral vector particles or virus like particles thereof, wherein said packaging cell line is negative for Low-Density Lipoprotein Receptor (LDLR), optionally said packaging cell line stably expresses VSV-G. A method for producing said VSV-G pseudotyped retroviral vector particles or virus like particles thereof is disclosed as well as said particles obtained by said method.

24 Claims, 10 Drawing Sheets

(56) References Cited

OTHER PUBLICATIONS

Rodrigues et al., Production of Retroviral and Lentiviral Gene Therapy Vectors: Challenges in the Manufacturing of Lipid Enveloped Virus, Viral Gene Therapy, Jul. 2011, pp. 15-40.
International Application No. PCT/EP2019/072931, International Search Report mailed Oct. 18, 2019, p. 4.
International Application No. PCT/EP2019/072931, International Preliminary Report on Patentability dated Mar. 2, 2021.

* cited by examiner

LDLR NEGATIVE PACKAGING CELL LINE FOR THE PRODUCTION OF VSV-G PSEUDOTYPED RETROVIRAL VECTOR PARTICLES OR VIRUS PARTICLES THEREOF

REFERENCE TO RELATED APPLICATIONS

This application is the U.S. National Stage of international application PCT/EP2019/072931, filed Aug. 28, 2019 (pending) and published on Mar. 5, 2020 as WO 2020/043765; which claims the priority benefit of EP application 18191784.0. The PCT application is hereby incorporated herein by reference in its entirety for all purposes.

FIELD OF THE INVENTION

The present invention relates to the field of packaging cell lines for production of retroviral vector particles or virus like particles thereof, especially for packaging cell lines that do not express the Low-Density Lipoprotein Receptor (LDLR) on their surface for the production of VSV-G pseudotyped retroviral vector particles or vectorlike particles (VLP) thereof.

BACKGROUND OF THE INVENTION

In the field of T and stem cell gene therapy, retroviral vectors such as lentiviral vectors (LV) are considered a highly efficient tool to deliver therapeutic nucleic acid molecules to target cells and induce long-term expression. Usually, retroviral vectors contain heterologous envelope proteins from foreign virus species within the retroviral membrane. The process of exchanging viral vector envelope proteins is called "pseudotyping". The most commonly used envelope protein for pseudotyping is the G protein of the Vesicular Stomatitis Virus (VSV-G). It transduces a broad range of target cells including therapeutic relevant cell types like stem cells and T cells. Binding of the trimeric VSV-G protein to its receptors induces multiple conformational changes from the pre-fusion to the post fusion state to catalyze the insertion of a hydrophobic fusion peptide to the target cell membrane and subsequent fusion of viral and target cell membrane. This process is pH dependent meaning that fusion of the viral and cellular membrane takes place predominantly in the endosome.

Before 2013, the attempts to identify the VSV-G receptor were not conclusive. For example, it has been proposed that the receptor is a phospholipid and not a protein. Then, Finkelshtein et al, Amirache et al and Nikolic et al have confirmed that LDLR is the main receptor of VSV-G. In addition, related family members of LDLR (i.e. LRP1, LRP1b, LRP2, LRP4, LRP5 und LRP6, VLDLR, LRP8) contribute to VSV mediated binding and infection as well. LDLR is a type 1 transmembrane glycoprotein and responsible for the regulation of cholesterol homeostasis in mammals. Loss-of-function mutations of the LDLR gene are associated with impaired delivery of cholesterol-rich LDL from the blood to the cells, which may result in familial hypercholesterolaemia in human. LDL is bound under neutral pH, followed by receptor-ligand internalization which finally leads to the release of the ligand in the endosome under acidic conditions. Afterwards the receptor is recycled back to the cell surface. Otahal et al has confirmed that the ligand-binding domain of LDLR plays a critical role for VSV-G interaction. Nikolic et al more specifically identified two distinct cysteine rich domains (CR2 and CR3) being responsible for binding to VSV-G as well. Related CR domains are also found in the VLDLR, LRP1, LRP1B, LRP2, LRP3, LRP4 (Nikolic et al). For enveloped viral particles like lentiviral vectors sufficient supply with lipids and the lipid composition of the packaging cell membrane are critical parameters of the infectivity and the yield of the viral particles (Guyader et al).

State-of-the-art protocols for VSV-G pseudotyped retroviral vectors are based on packaging cells like HEK 293 cells and its derivatives. These packaging cells are mainly cultivated in adherent cultivation vessels like roller bottles or cell factories but suspension cell cultures are of great interest to address limitations in scalability.

Stable packaging cells for VSV-G pseudotyped retroviral vectors continuously expressing some or all components are not available so far. This is attributed to the well-known toxicity of VSV-G (Rodrigues, Alves and Coroadinha); Thus, transient protocols have been established in the field that are based on transfecting packaging cells with 3-5 plasmids encoding all components (Merten et al). This approach enables a high level of flexibility by simply exchanging the required plasmids. However the reproducibility in yield from lot to lot is rather low due to variations in transfection efficiencies.

To avoid transfection procedures but to enable a high level of reproducibility, inducible systems have been established in the art to restrict expression of the toxic VSV-G protein to the harvesting period only. These systems require sophisticated transcriptional control expression cassettes and substances specifically inducing or shutting down the transcription of the gene of choice. Most systems make use of Tet-On/Tet-Off systems but alternative systems based on e.g. hormones are reported as well. These systems do not solve the problem of cytotoxicity but avoid the need of transient transfection and limit the burden of VSV-G toxicity to the harvesting period only. However, additional purification might be needed for therapeutic application to deplete the substance from the viral harvest. In addition, inducible or stable producing systems typically require large screening campaigns to identify packaging cell clones expressing all components at an optimal ratio to harvest high yields of retroviral vectors.

Thus, there is a need in the art for an improved or alternative packaging cell line for the production of VSV-G pseudotyped retroviral vector particles or virus like particles thereof and for the VSV-G pseudotyped retroviral vector particles or virus like particles thereof produced by said packaging cell line.

SUMMARY OF THE INVENTION

Surprisingly, the inventors found that a packaging cell line for the production of VSV-G pseudotyped retroviral vector particles or virus like particles thereof leads to higher yields of VSV-G pseudotyped retroviral vector particles or virus like particles thereof when said packaging cell line naturally or genetically engineered does not express the LDLR, i.e. the packaging cell line is negative for LDLR, as compared to a packaging cell line that expresses LDLR (an LDLR positive packaging cell line; e.g. HEK 293T WT). Said VSV-G pseudotyped retroviral vector particles or virus like particles may be VSV-G pseudotyped lentiviral vector particles or virus like particles and/or VSV-G pseudotyped gamma-retroviral vector particles or virus like particles.

Unexpectedly, the autotransduction of HEK 293 T cells negative for LDLR (HEK 293 T LDLR neg) with VSV-G pseudotyped retroviral vector particles or virus like particles thereof produced by said packaging cell line is up to 45% lower than the autotransduction when HEK 293T wild type (WT) is used as packaging cell line. As a consequence, the amount of harvestable VSV-G pseudotyped retroviral vector particles or virus like particles thereof is increased when an LDLR negative packaging cell line is used instead of an LDLR positive packaging cell line.

It could be shown that the same retroviral vector dose of VSV-G pseudotyped retroviral vector particles or virus like particles thereof derived from HEK 293T WT or HEK 293T LDLR negative packaging cells results in equal transduction rates on HEK 293T WT cells and on primary human T cells. In contrast, the addition of the same retroviral vector dose of VSV-G pseudotyped retroviral vector particles or virus like particles thereof results in lower transduction rates on HEK 293T LDLR negative cells for VSV-G pseudotyped retroviral vector particles or virus like particles thereof derived from HEK 293T LDLR negative packaging cells as compared to HEK 293T WT cells (see Example 5 and FIG. 7).

Therefore, a packaging cell line that naturally or genetically engineered does not express the LDLR on its cell surface is better suited for production of VSV-G pseudotyped retroviral vector particles or virus like particles thereof than packaging cell lines that express LDLR.

Exemplary, the surprising effect was demonstrated with the packaging cell line HEK 293T that normally express LDLR on its surface but was genetically engineered to prevent expression.

Surprisingly, the number and size of aggregates containing multiple particles of VSV-G pseudotyped retroviral vectors or virus like particles thereof derived from LDLR negative packaging cells is lower as compared to LDLR expressing packaging cells (see FIG. 6). This is an advantage to avoid loss of retroviral vectors or VLPs during purification and/or concentration when e.g. filtration steps with membranes of limiting pore size are applied. In addition, the yield of extractable retroviral vectors or VLPs is higher when the same number of retroviral vector particles or VLPs is present but to lower extent as aggregates containing multiple particles. Furthermore, aggregated retroviral vectors particles or VLPs may induce too high rates of VLP uptake or transduction potentially at levels inducing dose effects. For example, the number of retroviral vector genome integrations per host cell genome is higher if aggregates of particles are applied as compared to retroviral vector particles preferentially not present as aggregate.

In addition surprisingly, the toxic activity of VSV-G is less pronounced or even absent on LDLR negative packaging cell lines such as HEK 293T LDLR neg compared to LDLR positive packaging cell lines such as HEK 293T WT for transient and stable VSV-G expression. In consequence once VSV-G is expressed the viability of LDLR negative packaging cell lines such as HEK 293T LDLR neg is higher than for LDLR positive packaging cell lines such as HEK 293T WT. The viability of VSV-G expressing LDLR negative packaging cell lines such as HEK 293T LDLR-neg packaging cells is comparable to packaging cells that are not expressing VSV-G (see FIG. 5, FIG. 9A).

Therefore, the present invention comprises LDLR negative packaging cell lines for more efficiently producing VSV-G pseudotyped retroviral vector particles or virus like particles thereof, LDLR negative packaging cell lines that stably express VSV-G, a method for producing VSV-G pseudotyped retroviral vector particles or virus like particles thereof, and VSV-G pseudotyped retroviral vector particles or virus like particles thereof obtained by said method and/or produced by said LDLR negative packaging cell line.

BRIEF DESCRIPTION OF THE DRAWINGS

FIGS. A1 and B1: Principle of reducing autotransduction during the production of VSV-G pseudotyped LVs. A) HEK 293T WT cells package and release LVs into the cell culture supernatant but the dose of harvestable LVs is limited by losing LVs by transduction of the packaging cells. B) In contrast, the absence of LDLR on the packaging cell reduces the transduction rate and increases the dose of harvestable LVs.

HEK 293T WT cells were genetically modified to generate HEK 293T LDLR neg. The initial efficiency of 25% was increased to 90% by flow cytometric based cell sorting. Single cell cloning was subsequently performed to obtain homogenous, 100% pure HEK 293T LDLR neg clones (clone 1A1) that show improved LV productivity.

Figure 1:
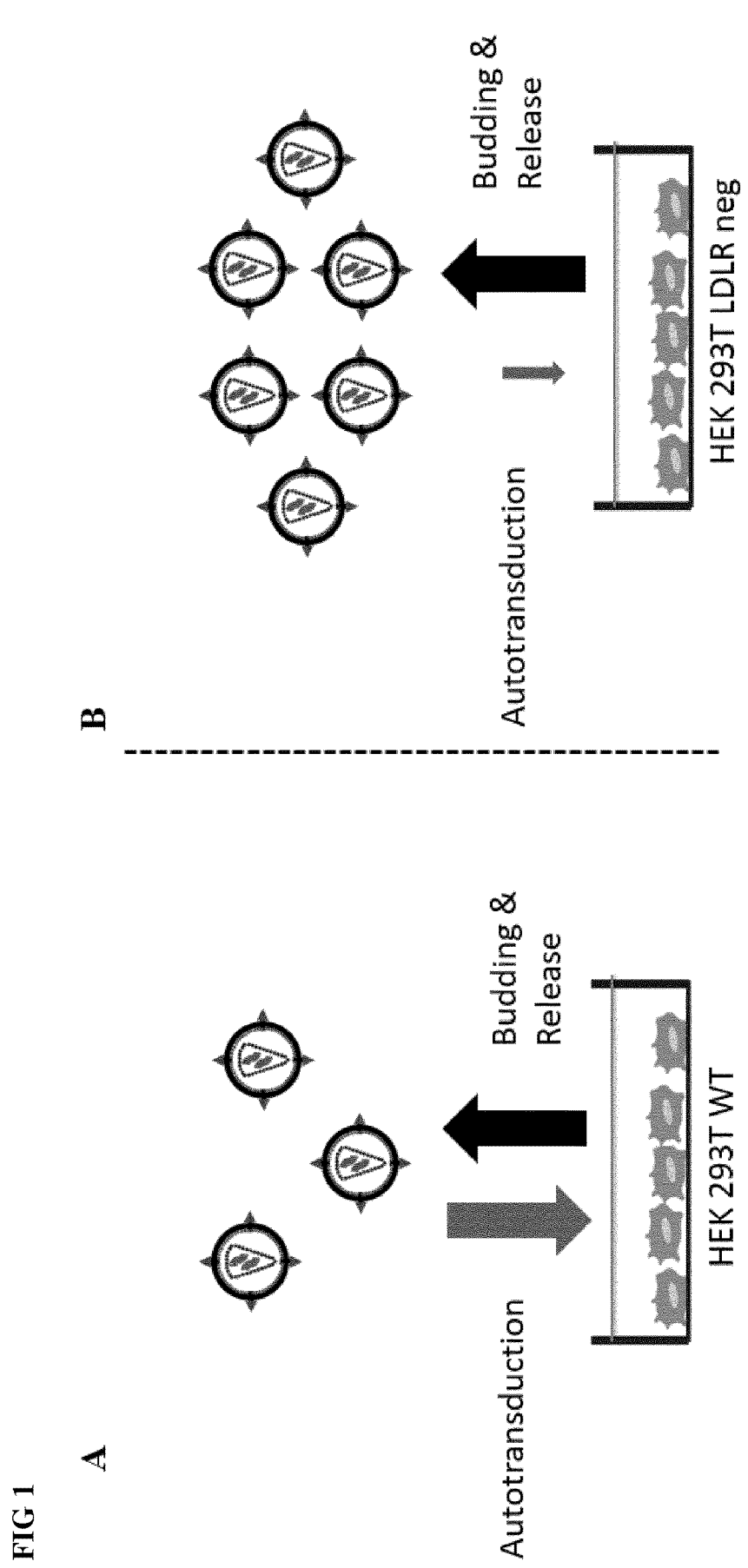
Figure 2:
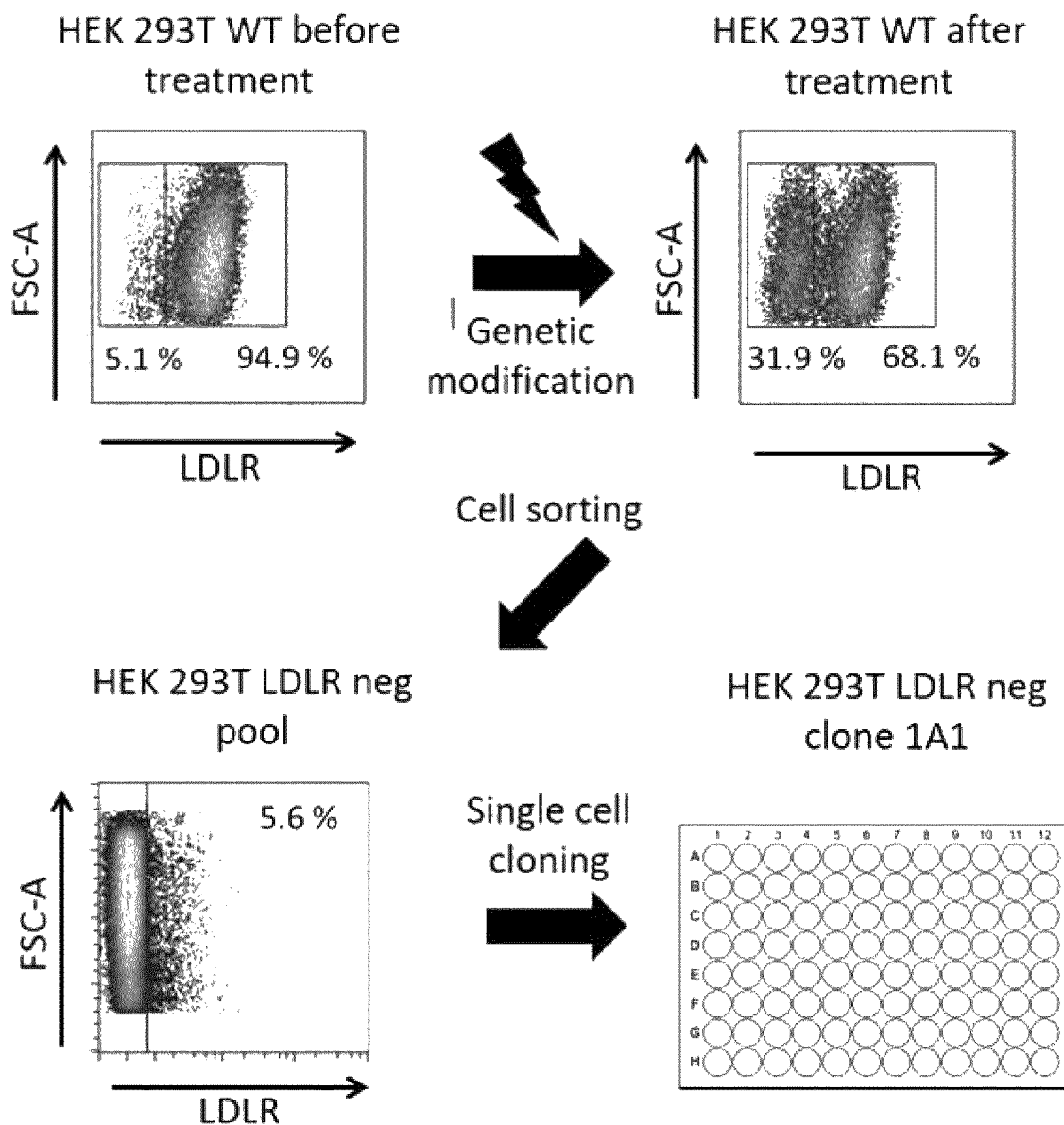
FIG. 2: Generation of LDLR deficient HEK 293T
Figure 3:
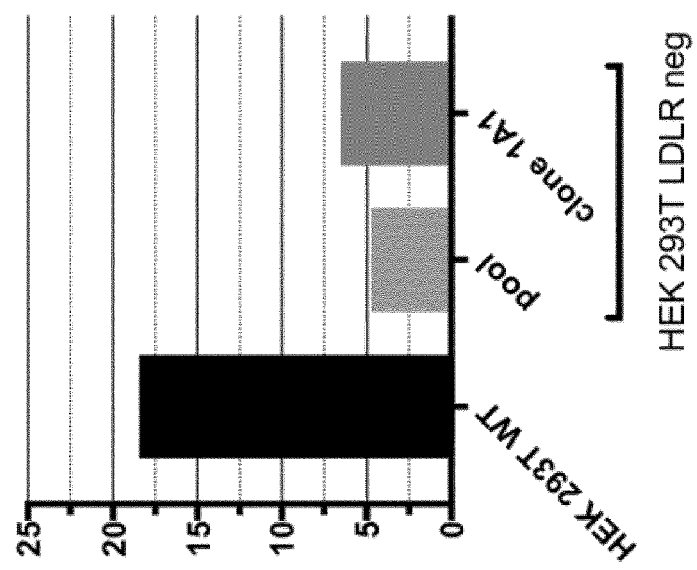
Figure 3:
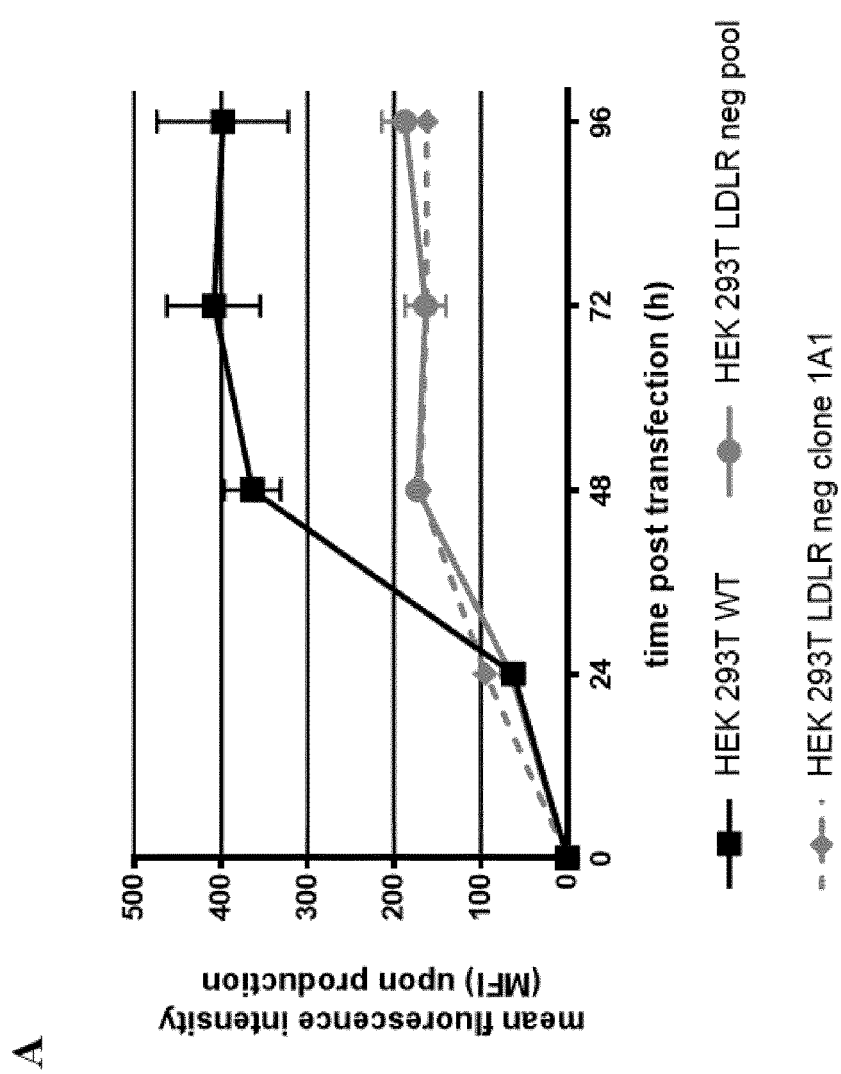

FIGS. 3A and 3B: Lower autotransduction rates by using HEK 293T LDLR neg packaging cells (pool and clone 1A1) as compared to HEK 293T WT.

A) Autotransduction was quantified by flow cytometry as stable and increasing mean of fluorescence intensity levels (MFI) upon transient transfection of HEK 293T WT, HEK 293T LDLR neg (pool and clone 1A1) to generate GFP encoding LVs. The rate of autotransduction on HEK 293T LDLR neg is reduced as compared to HEK 293T WT.

B) Autotransduction was confirmed by quantifying LV genomes copy numbers integrated into the host cell genome. 10 days post LV production, qPCR analysis was performed on genomic DNA isolated from transiently transfected HEK 293T, HEK 293T LDLR neg (pool and clone 1A1) to generate LVs. The number of integrated LV genome copy numbers is reduced on HEK 293T LDLR neg as compared to HEK 293T WT. The transfected packaging cells were cultivated for 10 additional days to exclude false-positive signals by diluting remaining plasmid DNA.

Figure 4:
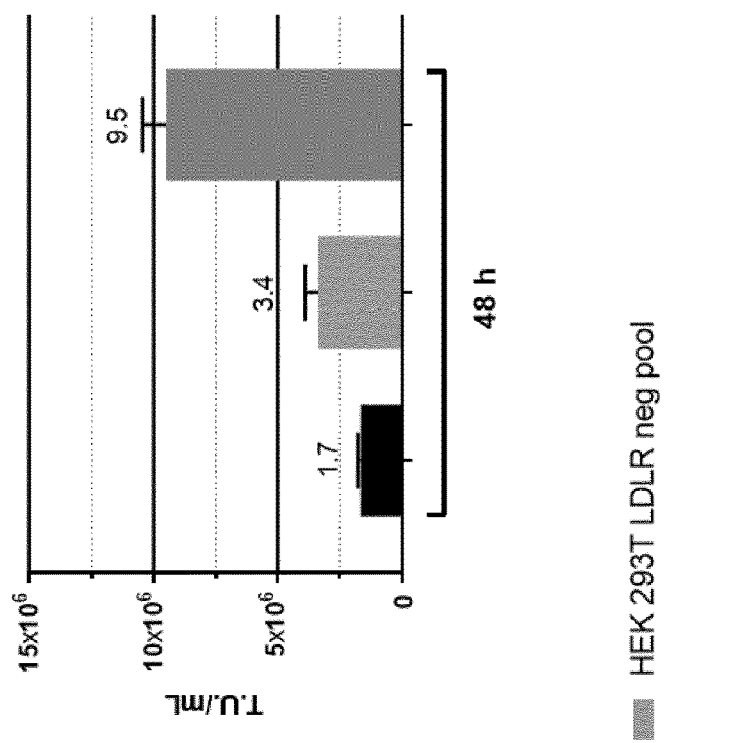
Figure 4:
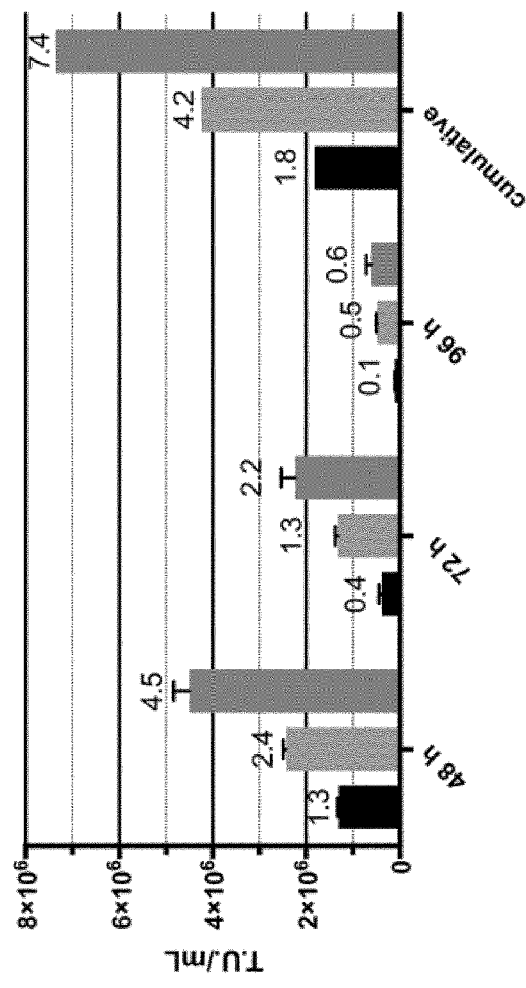

FIGS. 4A and 4B: Higher productivity by using HEK 293T LDLR neg (pool and clone 1A1) packaging cells as compared to HEK 293T WT packaging cells. The respective packaging cell line was transiently transfected with plasmids encoding for VSV-G, the gag/pol, rev and the LV transfer vector genome encoding a therapeutically active CD20-CAR construct (A) or GFP marker gene (B). The productivity was quantified by determining the LV titer at the indicated time post transfection and cumulated for all time points.

Figure 5:
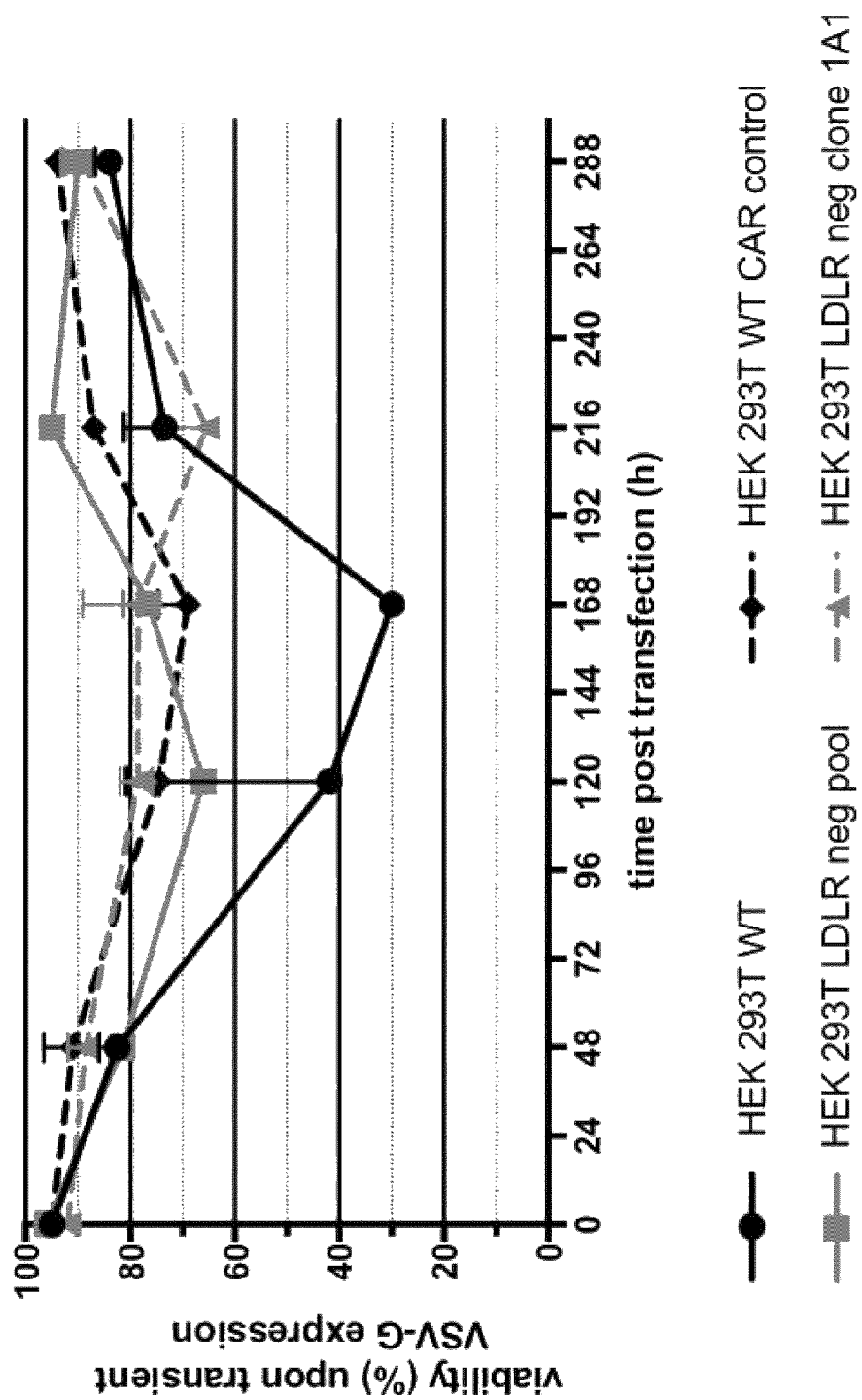

FIG. 5: Reduced toxicity of VSV-G upon transient expression in HEK 293T LDLR neg (pool and clone 1A1) as compared to HEK 293T WT. As control a CD20-specific CAR encoding plasmid was used. The viability (%) was measured for 288h in 48h interval.

Figure 6:
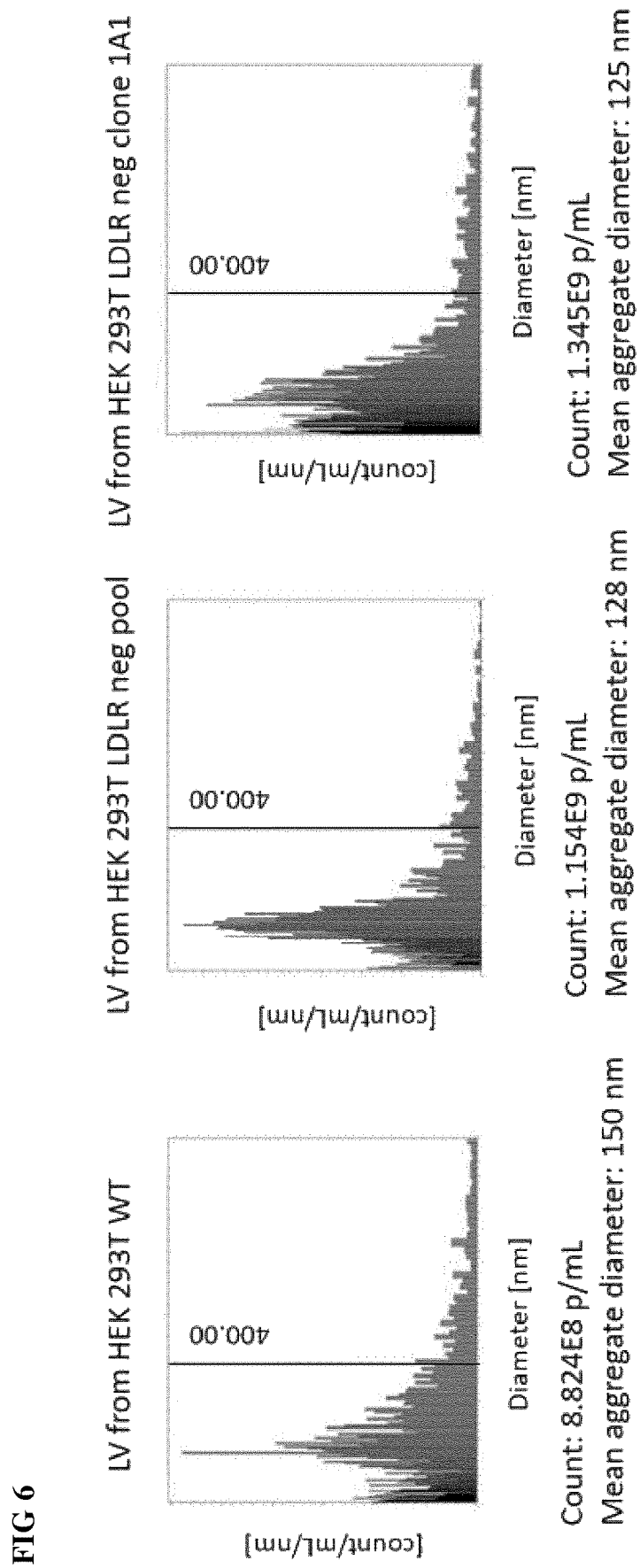

FIG. 6: Reduced LV aggregate formation for LVs produced in HEK 293T LDLR neg (pool and clone 1A1) as compared to HEK 293T WT. Aggregate formation of LVs present in the supernatant of the respective packaging cell line is determined by measuring the number of particles [count/mL/nm] and the corresponding particle diameter [in nm] using the Viewsizer 2000 (Manta Instruments).

Figure 7:
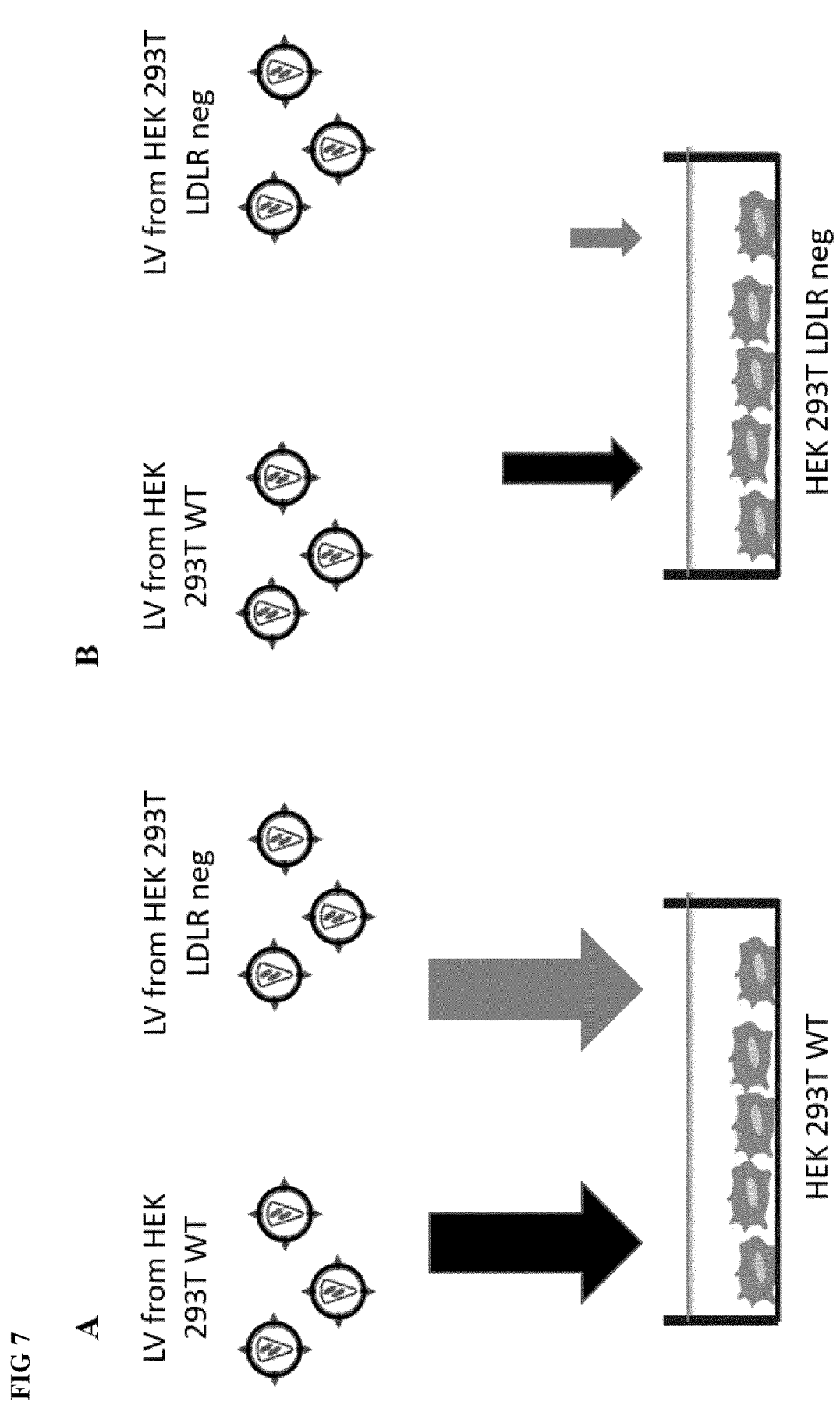

FIGS. 7A and 7B: Schematic drawing: LDLR expression levels of the cell line to be transduced but to a minor extent also the LDLR expression levels of the LV packaging cell line the LV is derived from determine the transduction efficiency levels during the production process. A) On HEK 293T WT the LDLR expression levels of the LV packaging cell line has no impact on the transduction efficiency levels. B) In contrast, the transduction efficiency levels on HEK 293T LDLR neg target cells is greatly reduced as compared to HEK 293T WT target cells and dependent on the LV packaging cell line as well.

Figure 8:
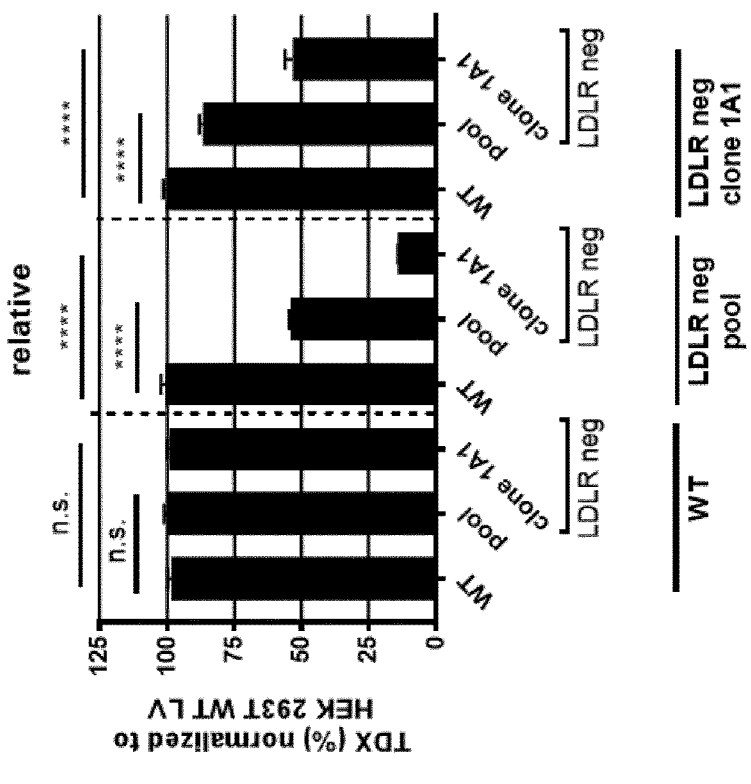
Figure 8:
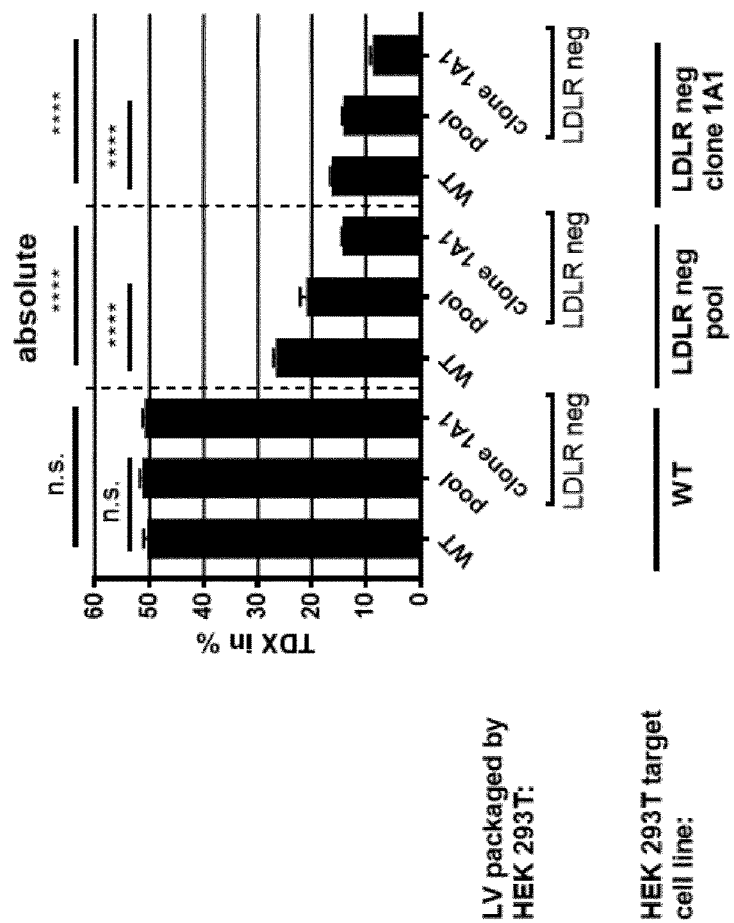

FIGS. 8A and 8B: A) Experimental results showing that LDLR expression levels of the cell line to be transduced but to a minor extent also the LDLR expression levels of the LV packaging cell line the LV is derived from determine the absolute transduction efficiency (TDX) levels during the production process. B) TDX levels normalized to the levels of HEK293T WT used packaging cell line. The experiment was performed three times in triplicates. One representative experiment out of three is shown. Statistical analysis based on unpaired Student t test (Prism,GraphPad). >0.05 (n.s.), <0.05 (*), <0.01 (), <0.001 (*), <0.0001 (****).

Figure 9:
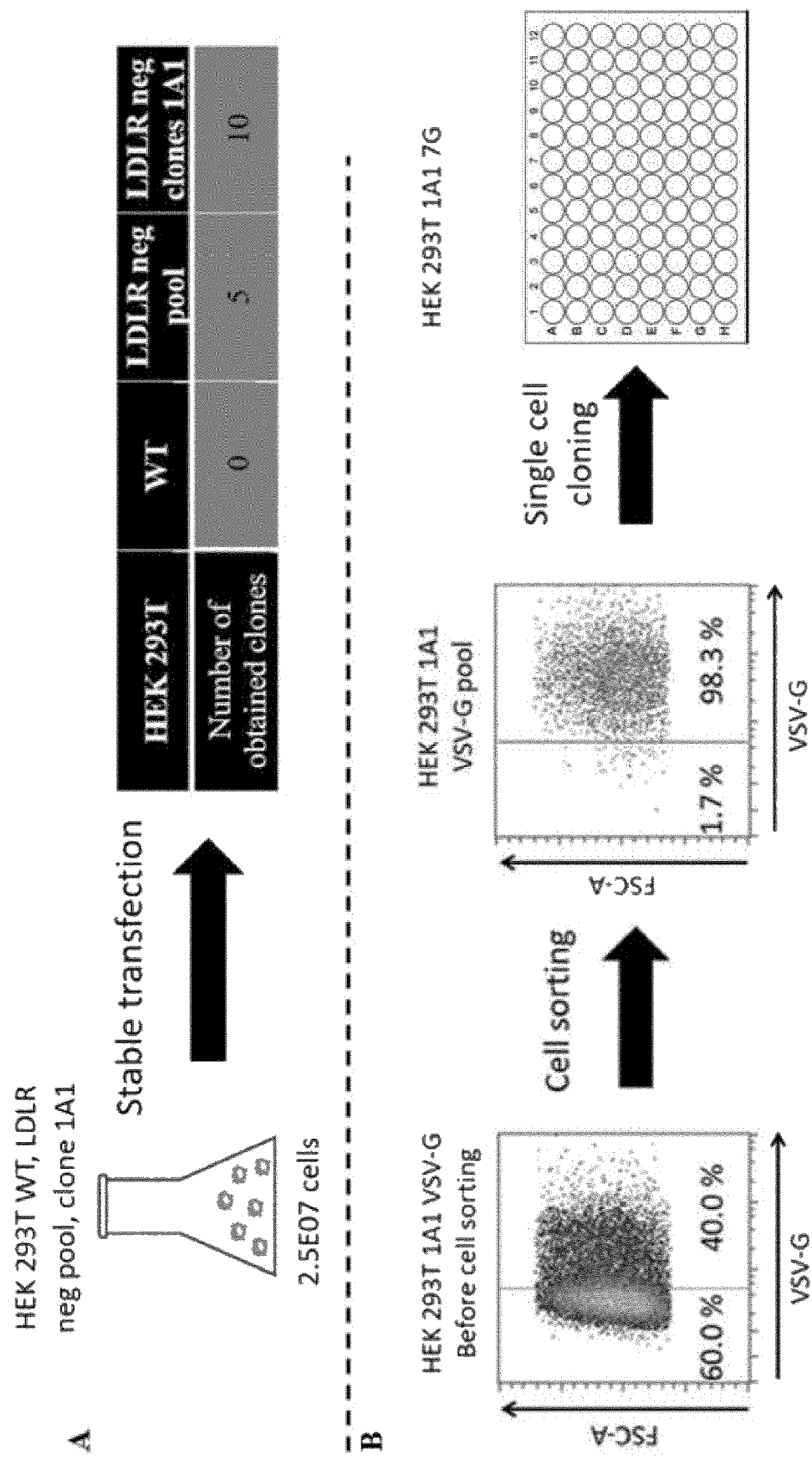

FIGS. 9A and 9B: Novel approach for generating LV packaging cell lines stably expressing VSV-G without transcriptional control or inducible system respectively. A) HEK 293T WT and HEK293T LDLR neg cells (HEK 293T LDLR neg pool or HEK 293T 1A1) were transfected with a plasmid encoding for VSV-G and an antibiotic (puromycin) resistance gene to select for stably transfected cells. After 34 days of cultivation in the presence of the antibiotic viable cell clones were only obtained for stably transfected HEK 293T LDLR neg packaging cells. B) Further experiments were performed with HEK 293T LDLR neg clone 1A1 (HEK 293T 1A1) stably transfected with VSV-G (Viability [V]: 89%). Flow cytometric cell sorting was applied to obtain packaging cells stably expressing VSV-G at high levels (HEK 293T 1A1 VSV-G pool). Finally, high producer cell clones were obtained by single cell cloning.

Figure 10:
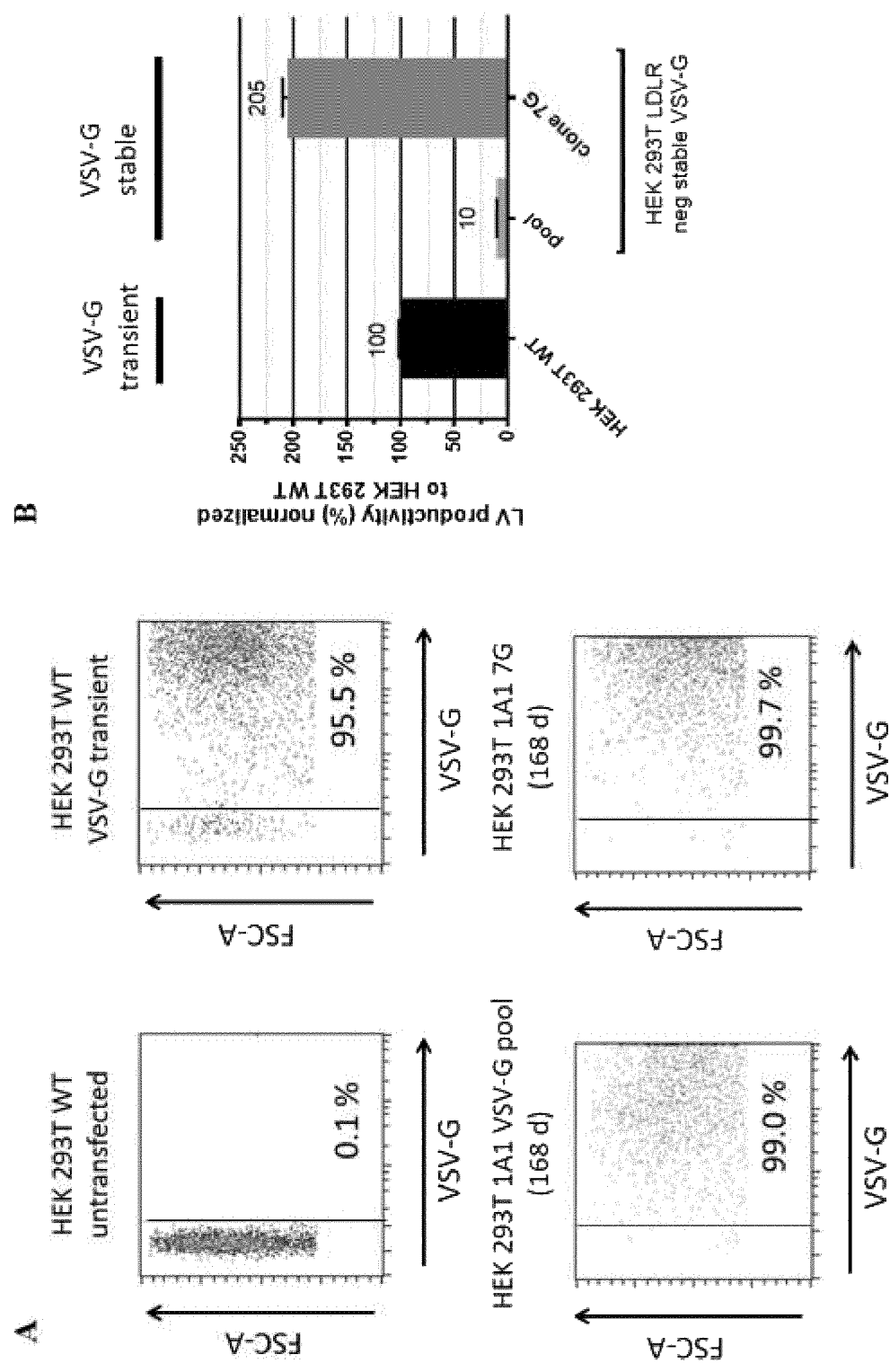

FIGS. 10A and 10B: Long-term VSV-G expression of viable and expanding HEK 293T 1A1 VSV-G pool and HEK 293T 1A1 7G and generation of functional LVs. A) VSV-G expression levels of untransfected HEK 293T WT and HEK 293T WT transiently transfected with the VSV-G encoding plasmid. For the packaging cells stably expressing VSV-G the expression levels are shown for HEK 293T 1A1 VSV-G pool and single cell clone HEK 293T 1A1 7G 168 days post transfection B) Packaging cells stably expressing VSV-G produce functional LVs. HEK 293T WT were transfected with all components required to generate LVs (full LV plasmid system; VSV-G, gag/pol, rev, GFP encoding transfer construct). As comparison, the packaging cell lines stably expressing VSV-G, HEK 293T 1A1 VSV-G pool and HEK 293T 1A1 7G were transfected with all components without the envelope plasmid VSV-G. The productivity is determined by measuring transducing units/mL (t.u./mL).

DETAILED DESCRIPTION OF THE INVENTION

In a first aspect the present invention provides a packaging cell line for the production of VSV-G pseudotyped retroviral vector particles or virus like particles thereof, wherein said packaging cell line is negative for LDLR.

Said packaging cell line for the production of VSV-G pseudotyped retroviral vector particles or virus like particles thereof, wherein said packaging cell line is negative for LDLR, thereby reducing autotransduction of said packaging cell line with VSV-G pseudotyped retroviral vector particles or virus like particles thereof produced by said packaging cell line for at least 20%, 25%, 30%, 35%, 40%, 45%, 50%, 55%, 60%, 65%, or 70% compared to autotransduction of a packaging cell line that is positive for LDLR.

Said packaging cell line may be a cell line that does not express originally or naturally LDLR, e.g. in its wild type format, on its cell surface.

Said packaging cell line may be a cell line that expresses originally or naturally LDLR, e.g. in its wild type format, on its cell surface but natural occurring variants (e.g. single cell clones) have been isolated that are negative for LDLR.

Said packaging cell line may be a cell line that express originally or naturally LDLR, e.g. in its wild type format, on its cell surface but chemical compounds are supplemented to the cell culture media that are known to prevent expression or activity or reduce the stability of the LDLR.

Said packaging cell line may be a cell line that expresses originally or naturally LDLR, e.g. in its wild type format, on its cell surface but may be genetically engineered (modified) to prevent expression of LDLR on its cell surface, i.e. it is modified to be negative for LDLR.

Therefore said packaging cell line may be a packaging cell line, wherein said packaging cell line has been genetically engineered to prevent expression of LDLR on its cell surface.

Said genetically modification may be achieved on genomic level e.g. by partially or completely modifying transcriptional control elements or the protein coding region of the LDLR gene. Methods needed for such modifications are well-known in the art and comprise technologies e.g. CrispR/Cas, TALEn, ZFN, homologous recombination.

Said packaging cell line may be a cell line that expresses originally or naturally LDLR, e.g. in its wild type format, on its cell surface but the expression of LDLR is inhibited on transcriptional level by using e.g. RNAi or epigenetic silencing.

Said packaging cell line may be a cell line for the production of VSV-G pseudotyped retroviralviral vector particles or virus like particles thereof, wherein said packaging cell line is negative for LDLR, thereby the mean aggregate size of said VSV-G pseudotyped retroviral vector particles or virus like particles is smaller as compared to the mean aggregate size of VSV-G pseudotyped retroviral vector particles or virus like particles derived from a packaging cell line expressing the LDLR.

The terms "negative for LDLR" or "LDLR neg" and the like in the context of methods for silencing or reducing the expression level of the gene LDLR refer herein also to a sufficient strong reduction of the expression of the gene LDLR in the packaging cell line achieved by said method so that the effect disclosed herein for a packaging cell line that is LDLR negative also appears and occurs for a packaging cell that has reduced expression levels of LDLR compared to the non-reduced state of said packaging cell line.

Said packaging cell line may be preferentially a human packaging cell line.

Said packaging cell line may be a HEK 293 cell or its derivatives, or a CEVEC amniocyte production (CAP) cell or its derivatives, or the cell line AGE1.HN or the cell line PER.C6.

Said packaging cell line may be selected from the group consisting of HEK 293, HEK 293T, HEK EBNA, HEK 293F, HEK 293FT, HEK 293-S, CEVEC amniocyte production (CAP) cell (CAP), CAP-T cell, CAP-GT cell and CAP-Go cell.

Said packaging cell line may be selected from the group consisting of HEK 293, HEK 293T, HEK EBNA, HEK 293F, HEK 293FT and HEK 293-S.

Said VSV-G pseudotyped retroviral vector particles or virus like particles may be VSV-G pseudotyped lentiviral vector particles or virus like particles and/or VSV-G pseudotyped gamma-retroviral vector particles or virus like particles.

Said packaging cell line, wherein said packaging cell line transiently expresses the gene VSV-G.

Said packaging cell line, wherein said packaging cell line stably expresses the gene VSV-G.

Said packaging cell line, wherein said packaging cell line stably expresses at least one additional gene selected from the group consisting of gag, pol, rev, and psi-positive retroviral expression vector encoding for a transgene.

Said packaging cell line, wherein said packaging cell line stably expresses all genes selected from the group consisting of gag, pol, rev, and a psi-positive lentiviral expression vector encoding for a transgene.

Said packaging cell line, wherein said packaging cell line stably expresses all genes selected from the group consisting of gag, pol, and a psi-positive gammaretroviral expression vector encoding for a transgene.

Said packaging cell line may be a producer cell line stably transfected with
  a) a psi-negative retroviral expression vector encoding for gag/pol genes, a psi-negative retroviral expression vector encoding for a rev gene if the retroviral expression vector is a lentiviral expression vector, a psi-positive retroviral expression vector encoding for a transgene and a psi-negative expression vector encoding for VSV-G, or
  b) a psi-negative retroviral expression vector encoding for gag/pol, a psi-negative retroviral expression vector encoding for rev if the retroviral expression vector is a lentiviral expression vector, a psi-positive retroviral expression vector encoding for a transgene and a psi-negative expression vector encoding for VSV-G.

Said producer cell line may also comprise a nucleic acid encoding for an antibiotic resistance gene such as neomycin-, hygromycin B-, Zeocin-, puromycin-resistance genes that may be on one of said expression vectors.

Said packaging cell line, wherein said cell line is negative for at least one additional receptor of VSV-G selected from the group consisting of LRP1, LRP1b, LRP2. LRP4, LRP5, LPR6, VLDLR and LRP8.

Said packaging cell line may be a cell line that is naturally negative for at least one additional receptor of VSV-G.

Said packaging cell line may be a cell line that may express originally said at least one additional receptor of VSV-G, e.g. in its wild type format, on its cell surface but may be genetically engineered (modified) to prevent expression of said at least one additional receptor of VSV-G on its cell surface, i.e. it is modified to be negative for said at least one additional receptor of VSV-G, therefore said packaging cell line may be a packaging cell line, wherein said packaging cell line has been genetically engineered (e.g. by methods described herein) to prevent expression of said at least one additional receptor of VSV-G on its cell surface.

Said packaging cell line, wherein said reduction of autotransduction is at least 20%, 25%, 30%, 35%, 40%, 45%, 50%, 55%, 60%, 65%, or 70% compared to the autotransduction of a packaging cell line that is not LDLR negative.

Said packaging cell line, wherein said VSV-G pseudotyped retroviral vector particles or virus like particles comprise a transgene.

Said transgene may be any gene that that should be introduced into a target cell that is intended to be transduced by VSV-G pseudotyped retroviral vector particle or virus like particle thereof produced as disclosed herein. That transgene then may be expressed by said target cell. Said transgene may be a gene encoding for a marker gene, for a therapeutic protein e.g. a chimeric antigen receptor (CAR) that is expressed in or on a target cell, e.g. an immune cell such as a T cell or NK cell or for a non-mutated allele of a monogenic disease such as Beta-thalassemia, SCID-X1, Wiskott-Aldrich syndrome, thereby correcting the defective stem cell to be a non-defective cell.

In another aspect the present invention provides the use of a packaging cell line as disclosed herein for the production of VSV-G pseudotyped retroviral vector particles or virus like particles thereof, wherein said packaging cell line is negative for LDLR.

In one aspect the present invention provides the use of a packaging cell line for the production of VSV-G pseudotyped retroviral vector particles or virus like particles thereof, as disclosed herein, wherein said packaging cell line stably expresses VSV-G.

In a further aspect the present invention provides an in-vitro method for producing VSV-G pseudotyped retroviral vector particles or virus like particles thereof, the method comprising
  a) providing a packaging cell line, wherein said packaging cell line is negative for LDLR as disclosed herein
  b) introducing into said cell psi-negative nucleic acids at least encoding for gag/pol, psi-negative nucleic acids encoding for rev if the retroviral expression vector is a lentiviral expression vector, and psi-negative nucleic acids encoding for VSV-G and a psi-positive nucleic acid encoding for a transgene, thereby producing said VSV-G pseudotyped retroviral vector particles or virus like particles thereof.

Said produced VSV-G pseudotyped retroviral vector particles or virus like particles thereof reduce the autotransduction of said packaging cell line with said VSV-G pseudotyped retroviral vector particles or virus like particles thereof for at least 20%, 25%, 30%, 35%, 40%, 45%, 50%, 55%, 60%, 65%, or 70% compared to the autotransduction of a packaging cell line that is positive for LDLR. Said VSV-G pseudotyped retroviral vector particles or virus like particles may be VSV-G pseudotyped lentiviral vector particles or virus like particles and/or VSV-G pseudotyped gammaretroviral vector particles or virus like particles.

Said method, wherein said packaging cell line is in a cell culture medium.

Said method, wherein said method additionally comprises
  c) isolating cell culture medium comprising said VSV-G pseudotyped retroviral vector particles or virus like particles thereof.

Said isolating cell culture medium comprising said VSV-G pseudotyped retroviral vector particles or virus like particles thereof may be performed by removing at least a part of the medium (the supernatant) that contains said VSV-G pseudotyped retroviral vector particles or virus like particles thereof, wherein said packaging cell line remains in the medium.

Said method, wherein said introducing of the nucleic acids is performed by
  i) co-transfecting of said packaging cell line with a psi-negative retroviral expression vector encoding for gag/pol, a psi-negative retroviral expression vector encoding for rev if the retroviral expression vector is a lentiviral expression vector, a psi-positive retroviral expression vector encoding for a transgene and a psi-negative expression vector encoding for VSV-G, or
  ii) co-transfecting of said packaging cell line with a psi-negative retroviral expression vector encoding for gag/pol rev, a psi-positive retroviral expression vector encoding for a transgene and a psi-negative expression vector encoding for VSV-G.

Additionally a nucleic acid encoding for an antibiotic resistance gene may be introduced during said co-transfection, wherein said resistance gene is on one of the expression vectors, thereby allowing to generate a stable packaging cell line. Genes encoding for antibiotic resistance suitable for cell selection are well-known in the art, and include e.g. neomycin-, hygromycin B-, Zeocin-, puromycin-resistance genes Other methods and technologies well known in the art may be used to introduce said nucleic acids into said packaging cell line. One other technology used may be the CRISPR/Cas9 technology. Therefore, said method may be used, wherein additionally a resistance gene may be introduced and wherein said introducing of said nucleic acids may be performed by directed integration of said nucleic acids into the genome of said cell using CRISPR/Cas9 technology, thereby allowing to generate a stable packaging cell line.

In another aspect the present invention provides an in-vitro method for producing VSV-G pseudotyped retroviral vector particles or virus like particles thereof, the method comprising
    a) providing a packaging cell line that stably expresses the gene VSV-G as disclosed herein
    b) introducing into said cell psi-negative nucleic acids encoding for gag/pol, a psi-negative retroviral expression vector encoding for rev if the retroviral expression vector is a lentiviral expression vector, and a psi-positive nucleic acid encoding for a transgene, thereby producing said VSV-G pseudotyped retroviral vector particles or virus like particles thereof.

Said method, wherein said packaging cell line is in a cell culture medium.

Said method, wherein said method additionally comprises
    c) isolating cell culture medium comprising said VSV-G pseudotyped retroviral vector particles or virus like particles thereof.

In a further aspect the present invention provides an in-vitro method for producing VSV-G pseudotyped retroviral vector particles or virus like particles thereof, the method comprising
    a) providing a packaging cell line that stably expresses the gene VSV-G, wherein said packaging cell line stably expresses at least one additional gene as disclosed herein selected from the group consisting of gag/pol, rev, and a transgene
    b) introducing into said the cell psi-negative nucleic acid(s) encoding for gag/pol, a psi-negative retroviral expression vector encoding for rev if the retroviral expression vector is a lentiviral expression vector, and a psi-positive nucleic acid encoding for a transgene, that is/are not stably expressed by said packaging cell line, thereby producing said VSV-G pseudotyped retroviral vector particles or virus like particles thereof.

Said method, wherein said packaging cell line is in a cell culture medium.

Said method, wherein said packaging cell line is in a cell culture medium that is serum free, Said method, wherein said packaging cell line is cultured in suspension.

Said method, wherein said method additionally comprises
    c) isolating cell culture medium comprising said VSV-G pseudotyped retroviral vector particles or virus like particles thereof.

Said method, wherein said packaging cell line (producer cell line) stably expresses all of said at least one additional gene selected from the group consisting of gag/pol, rev, and a transgene.

In a further aspect the present invention provides a VSV-G pseudotyped retroviral vector particle or virus like particle thereof obtainable by the methods as disclosed herein and/or produced by the packaging cell lines as disclosed herein.

Said VSV-G pseudotyped retroviral vector particle or virus like particle may be a VSV-G pseudotyped lentiviral vector particle or virus like particle and/or a VSV-G pseudotyped gamma-retroviral vector particle or virus like particle.

The VSV-G pseudotyped retroviral vector particle or virus like particle thereof obtained by the methods as disclosed herein and/or produced by the packaging cell lines as disclosed herein transduces packaging cell lines that are negative for LDLR with lower efficiency than a VSV-G pseudotyped retroviral vector particle or virus like particle thereof obtained by a packaging cell line that expresses LDLR.

The VSV-G pseudotyped retroviral vector particle or virus like particle thereof obtained by the methods as disclosed herein and/or produced by the packaging cell lines as disclosed herein have a mean aggregate size that is at least 5%, 10%, or 15% smaller compared to the mean aggregate size of VSV-G pseudotyped retroviral vector particles or virus like particles derived from a packaging cell line expressing the LDLR.

The VSV-G pseudotyped retroviral vector particle or virus like particle thereof obtained by the methods as disclosed herein and/or produced by the packaging cell lines as disclosed herein have a reduced level of aggregate formation of the retrovirus vector particle or virus like particle thereof compared to the mean aggregate size of VSV-G pseudotyped retroviral vector particles or virus like particles derived from a packaging cell line expressing the LDLR. The effect of reduced aggregate formation leads to the above mentioned smaller aggregate size of VSV-G pseudotyped retroviral vector particles or virus like particles as disclosed herein.

The use of the VSV-G pseudotyped retroviral vector particle or virus like particle thereof obtained by the methods as disclosed herein and/or produced by the packaging cell lines as disclosed herein allow a) to avoid the loss of retroviral vector particles or VLPs thereof during purification and/or concentration when e.g. filtration steps with membranes of limiting pore size are applied, b) to increase the yield of extractable retroviral vector particles or VLPs thereof when the same number of retroviral vector particles or VLPs thereof is present but to lower extent as aggregates, and c) to prevent dose effects such as a high number of retroviral vector genome integrations per host cell genome induced by aggregated retroviral vector particles or VLPs thereof.

In another aspect the present invention provides a pharmaceutical composition comprising the VSV-G pseudotyped retroviral vector particle or virus like particle thereof as disclosed herein, optionally further comprising a pharmaceutically acceptable carrier.

The use of the VSV-G pseudotyped retroviral vector particle or virus like particle thereof as disclosed herein as a pharmaceutical composition leads to less retroviral vector genome integrations per cell due to the reduced tendency of aggregation compared to VSV-G pseudotyped retroviral vector particle or virus like particle thereof that have been produced in LDLR positive cell lines.

In a further aspect the present invention provides the use of the VSV-G pseudotyped retroviral vector particle or virus like particle thereof as disclosed herein for the preparation of a medicament.

In another aspect, the present invention provides a packaging cell line for the production of pseudotyped retroviral vector particles or virus like particles thereof, wherein said packaging cell line is negative for Low-Density Lipoprotein Receptor (LDLR), and wherein said pseudotyped retroviral vector particles or virus like particles thereof are pseudotyped with an envelope protein other than VSV-G. For example, the said packaging cell line may be used for the production of retroviral vector particles or virus like particles thereof that are pseudotyped with alternative envelope proteins such as RD 114, GALV env, Measles virus H/F, Nipah virus G/F, Baboon env, Cocal env.

All definitions and embodiments defined herein with regard to the packaging cell line for production of VSV-G pseudotyped retroviral vector particles or virus like particles of the invention also apply mutatis mutandis in the context of the other aspects of the invention: e.g. the use of the packaging cell line for the production of VSV-G pseudotyped retroviral vector particles or virus like particles thereof,
a method for producing VSV-G pseudotyped retroviral vector particles or virus like particles thereof, a VSV-G pseudotyped retroviral vector particle or virus like particle thereof obtainable by the method as disclosed herein, a pharmaceutical composition comprising the VSV-G pseudotyped retroviral vector particle or virus like particle as disclosed herein, and a use of the VSV-G pseudotyped retroviral vector particle or virus like particle thereof as disclosed herein for the preparation of a medicament.

Embodiments

In one embodiment of the present invention the HEK 293T packaging cell line has been knocked out for the gene LDLR by methods well-known in the art resulting in a HEK 293T packaging cell line that is negative for the LDLR (HEK 293T K.O.) This HEK 293T K.O. packaging cell line is cotransfected with a psi-negative lentiviral expression vector encoding for gag/pol genes, a psi-negative lentiviral expression vector encoding for a rev gene, a psi-positive lentiviral expression vector encoding for a transgene and a psi-negative expression vector encoding for VSV-G, the transgene may encode for e.g. a chimeric antigen receptor. The HEK 293T K.O. packaging cell line produces a high rate of VSV-G pseudotyped lentiviral vector particles that bear the genetic information for a transgene, e.g. the chimeric antigen receptor. These particles may be used to transduce stem cells or immune cells such as T cells or NK cells to be intended to express the transgene, e.g. the chimeric antigen receptor.

In another embodiment of the invention the method for producing VSV-G pseudotyped retroviral vector particles, e.g. lentiviral vector particles or virus like particles thereof comprises
 a) co-transfection of a packaging cell line as disclosed herein with a psi-negative lentiviral expression vector encoding for gag/pol genes, a psi-negative lentiviral expression vector encoding for a rev gene, a psi-positive lentiviral expression vector encoding for a transgene and a psi-negative expression vector encoding for VSV-G, or
 b) co-transfection of a packaging cell line as disclosed herein with a psi-negative lentiviral expression vector encoding for gag/pol/rev genes, a psi-positive lentiviral expression vector encoding for a transgene and a psi-negative expression vector encoding for VSV-G, thereby reducing the autotransduction of said packaging cell line with the VSV-G pseudotyped lentiviral vector particles or virus like particles thereof produced by said packaging cell line.

The VSV-G pseudotyped lentiviral vector particles or virus like particles thereof produced by said packaging cell line may be harvested from the supernatant of the cell culture medium in which said packaging cell line is cultured.

In one embodiment of the invention the harvested supernatant containing VSV-G pseudotyped lentiviral vector particles or virus like particles thereof produced by said packaging cell line may be filtrated.

In another embodiment of the invention said packaging cell line is cultured serum-free and/or in suspension.

The packaging cell line may be a transiently expressing cell line or a stably expressing cell line, i.e. a producer cell line.

For establishing a stably expressing packaging cell line a nucleic acid encoding for an antibiotic resistance gene that is on one of said vectors is also co-transfected. Coexpression of this resistance gene allows for the selection of cells that stably express the VSV-G pseudotyped lentiviral vector particles or virus like particles as disclosed herein.

Definitions

Unless defined otherwise, technical and scientific terms used herein have the same meaning as commonly understood by one of ordinary skill in the art to which this invention belongs.

Retroviridae is virus family with a single-stranded, diploid, positive-sense RNA genome that is reverse-transcribed into a DNA intermediate that is then incorporated into the host cell genome.

Retroviridae-derived viruses are enveloped particles with a diameter of 80-120 nm. (Retro-/lenti-/gammaretro-) viral vectors are replication-deficient viral particles that are derived from the corresponding virus family. They contain gag and pol proteins, a single-stranded RNA genome and are usually pseudotyped with heterologous envelope proteins derived from other viruses. The RNA genome of said viral vectors do not contain any viral gene to produce viral progeny, but psi elements and LTRs that are required for efficient packing and reverse transcription in DNA. The DNA intermediate may contain a gene of interest under the control of a suitable promoter, for example, the CMV promoter and the gene of interest is expressed upon integration of said DNA into the genome of the host cell. The process of entering the host cell, delivering the RNA genome, integration and expression of the gene of interest is called transduction. The minimal requirements of a gammaretrovirus or lentivirus based viral vector has been well-described in the art.

In addition, integrase-deficient retroviral vectors (ID-RVs) have been developed that cannot integrate the retroviral vector genome in the host cell genome. ID-RVs are derived from conventional retroviral vectors but contain no or a mutated form of the retroviral integrase. Upon entry into the host cell, the retroviral vector genome is reverse-transcribed in the cytoplasm, delivered into the nucleus, but not stably integrated into the host cell genome. ID-RVs are a useful tools to express the gene of interest transiently. The definition of retroviral vectors and transduction also extents the integration-deficient retroviral vectors and its application.

Lentivirus is a genus of Retroviridae that cause chronic and deadly diseases characterized by long incubation periods, in the human and other mammalian species. The best-known lentivirus is the Human Immunodeficiency Virus HIV which can efficiently infect nondividing cells, so lentiviral derived retroviral vectors are one of the most efficient methods of gene delivery.

Gammaretroviridae is a genus of the Retroviridae family. Representative species are the murine leukemia virus and the feline leukemia virus.

The VSV-G pseudotyped retroviral vector particles or virus like particles used and disclosed herein may be VSV-G pseudotyped lentiviral vector particles or virus like particles and/or VSV-G pseudotyped gamma-retroviral vector particles or virus like particles.

Virus-like particles (VLPs) resemble viral particles, but are not infecting or transducing because they contain no viral genetic material encoding for the proteins of the virus-like particle. In particular, VLPs in the context of retroviral vectors do not contain psi positive nucleic acid molecules. Some virus-like particles may contain nucleic acid distinct from their genome. The expression of viral structural proteins, such as envelope or capsid, can result in the assembly of virus like particles (VLPs). Like for retroviral vectors VLPs can also be pseudotyped using the same envelope constructs as for retroviral vectors. VLPs may be used to deliver proteins but also nucleic acids to the cytoplasm of target cells. In particular, VLPs are useful as vaccines.

The term "pseudotyping" or "pseudotyped" as used herein refers to a vector particle bearing envelope glycoproteins derived from other viruses having envelopes. The host range of the retroviral vectors or vector particles of the present invention can thus be expanded or altered depending on the type of cell surface receptor used by the glycoprotein.

To generate retroviral vectors the gag/pol and env proteins needed to assemble the vector particle are provided in trans by means of a packaging cell line, for example, HEK 293T. This is usually accomplished by transfection of the packaging cell line with one or more plasmids containing the gag/pol and env genes. For the generation of pseudotyped vectors, the env gene, originally derived from the same retrovirus as the gag and pol genes and as the RNA molecule or expression vector, is exchanged for the envelope protein(s) of a different enveloped virus. As an example, VSV-G pseudotyped retroviral vector particle or virus like particle thereof refers to retroviral vectors or virus like particles that have incorporated the G protein of the vesicular stomatitis virus (VSV-G) into the membrane.

Thus, an exemplary pseudotyped vector particle based on the HIV-1 retrovirus comprises the (1) HIV-1 Gag and Pol proteins, (2) an RNA molecule derived from the HIV-1 genome that may be used to generate a retroviral vector particle based on the HIV-1 genome lacking the gag, env, pol, tat, vif, vpr, vpu and nef genes, but still comprising the LTRs, the psi element and a CMV promoter followed by the gene to be transduced, for example, a gene for the GFP protein, and (3) the G protein of the Vesicular Stomatitis Virus (VSV-G) is used.

The Vesicular Stomatitis Virus (VSV) is a species of the genus Vesiculovirus within the family Rhabdoviridae within the order Mononegavirales. The genome of VSV encodes for the G protein that is responsible for binding and entry of the virus into the target cell. It is a homotrimer that induces clathrin-mediated endocytosis in the endosome once the receptor has been bound on the cell surface. In the endosome, the pH shift induces a conformational change of the homotrimer inducing irreversible fusion of the viral and cellular membrane.

The terms "psi-positive" and "psi-negative", as used in the present application, refer to a nucleic acid molecule where the retroviral psi element is present and absent, respectively. The psi element is a cis-acting signal located near the 5' end of the retroviral genome and designates a packaging signal, which is of importance during assembly of the viruses and leads to the incorporation of the viral RNA into the viral core. Thus, a psi-negative RNA does not comprise the retroviral psi element and consequently will not be assembled into a vector particle of the present invention; in contrast, a psi-positive RNA that does comprise said psi element will be effectively assembled into the vector particle.

The terms "Titer" or "transduction efficiency" is used as a means to characterize and compare vector particles with regard to their ability to transduce their target cells. Thus, vector particles having an "increased titer" or an "increased transduction efficiency" are able to transduce a higher number of cells at a given vector particle volume than other vector particles with the same volume.

The term "a packaging cell line" as used herein refers to a cell line such as HEK 293 that is able to produce retroviral vector particles or virus like particles thereof. The packaging cell line may produce said retroviral vector particles or virus like particles thereof transiently or stably, depending on the kind of preparation of the cell line. Preferentially, the packaging cell line may be a human packaging cell line.

If the packaging cell line stably produces (generates) said retroviral vector particles or virus like particles thereof it may also be called as a "producer cell line".

The terms "negative for LDLR" or "LDLR neg" and the like in the context of a packaging cell line means that the gene LDLR is not expressed on the surface of said packaging cell lines or at least the expression level of LDLR is sufficiently strong reduced by methods of silencing or reducing expression levels of proteins by methods well-known in the art. The effects observed on packaging cell lines that do not express LDLR as disclosed herein also appear and occur on a packaging cell lines with sufficiently strong reduction of LDLR expression. The terms "negative for LDLR" or "LDLR neg" may also include packaging cell lines that have mutated forms of the LDLR with decreased or lost affinity to VSV-G, such as GM01915 fibroblasts. Said packaging cell line may be a cell line that is naturally negative for LDLR, but said packaging cell line may also be a cell line that may express originally LDLR, i.e. in its wild type format on its cell surface but may be genetically engineered (modified) to prevent expression of LDLR on its cell surface, i.e. it is modified to be negative for LDLR.

Said genetically modification may be achieved e.g. by recombinantly knocking out the LDLR, by deleting the LDLR, or by silencing the LDLR expression by using e.g. RNAi.

Said packaging cell line may be selected from the group consisting of HEK 293, HEK 293T, HEK EBNA, HEK 293F, HEK 293FT and HEK 293-S, wherein said cell lines are negative for LDLR.

The terms "negative for LDLR" and "LDLR negative" and "LDLR neg" and "LDLR$^-$" may be used interchangeably.

The terms "positive for LDLR" and "LDLR positive" and "LDLR pos" and "LDLR$^+$" in the context of a packaging cell line means that the gene LDLR is expressed on the surface of said packaging cell line.

The Low-Density Lipoprotein (LDL) Receptor (LDL-R or LDLR) is a mosaic protein of 839 amino acids (after removal of 21-amino acid signal peptide) that mediates the endocytosis of cholesterol-rich LDL. It is a cell-surface receptor that recognizes the apoprotein B100, which is embedded in the outer phospholipid layer of LDL particles. The receptor also recognizes the apoE protein found in chylomicron remnants and VLDL remnants (IDL). In humans, the LDL receptor protein is encoded by the LDLR gene on chromosome 19. It belongs to the Low density lipoprotein receptor gene family. LDLR is the putative main receptor of VSV-G.

The term "autotransduction" as used herein means the transduction of a packaging cell line that is producing retroviral vector particles or virus like particles thereof that transduce said packaging cell line. Autotransduction is induced by the expression of the receptor of pseudotyped retroviral vector particles or virus like particles thereof by the packaging cell line.

The term "reduction of autotransduction" as used herein means that the autotransduction of a packaging cell line that is LDLR negative is reduced compared to a packaging cell line that is positive for LDLR. The reduction of autotransduction of the packaging cell line as disclosed herein may be at least 20%, 25%, 30%, 35%, 40%, 45%, 50%, 55%, 60%, 65%, or 70% compared to the autotransduction of a packaging cell line that is not LDLR negative, i.e. that is LDLR positive.

The term "aggregate" as used herein refers to a physical structure of accumulated VSV-G pseudotyped retroviral vector particles or virus like particles containing at least two particles.

For example, the number and size of aggregates containing multiple particles of VSV-G pseudotyped retroviral vector particles or virus like particles thereof derived from LDLR negative packaging cells is lower as compared to LDLR expressing packaging cells.

The term "expression" as used herein is defined as the transcription and/or translation of a particular nucleotide sequence driven by its promoter in a cell.

The terms "(genetically) engineered cell" and "(genetically) modified cell" as used herein can be used interchangeably. The terms mean containing and/or expressing a foreign gene or nucleic acid sequence which in turn modifies the genotype or phenotype of the cell or its progeny The term "transgene" describes a segment of DNA containing a gene sequence that has been isolated from one organism and is introduced into a different organism. This non-native segment of DNA may either retain the ability to produce RNA or protein in the transgenic organism or alter the normal function of the transgenic organism's genetic code.

Human embryonic kidney cells 293, also often referred to as HEK 293, HEK-293, 293 cells, or less precisely as HEK cells, are a specific cell line originally derived from human embryonic kidney cells grown in tissue culture. HEK 293 cells have been widely used in cell biology research for many years, because of their reliable growth and propensity for transfection. They are also used by the biotechnology industry to produce therapeutic proteins and viruses for gene therapy.

An important variant of this cell line is the 293T cell line. It contains the SV40 Large T-antigen that allows for episomal replication of transfected plasmids containing the SV40 origin of replication. This allows for amplification of transfected plasmids and extended temporal expression of desired gene products. HEK 293, and especially HEK 293T, cells are commonly used for the production of various retroviral vectors. Various retroviral packaging cell lines are also based on these cells.

To summarize derivates of HEK 293 (original cell line) are e.g. HEK 293T (transforming HEK 293 with the simian virus 40 (SV40) large T antigen), HEK EBNA (HEK 293 cell line transformed with the Epstein Barr virus (EBV) nuclear antigen 1), HEK 293F and HEK 293FT (derived from HEK 293 cells), HEK 293-S (serumfree adapted HEK 293 cells). The HEK 293 or said derivates may be used in the present invention, wherein these cell lines have been genetically modified to prevent LDLR expression on their cell surfaces.

CEVEC amniocyte production cells (CAP), e.g. CAP cells, CAP-T cells, CAP-GT cells or CAP-Go cells were originally derived from primary human amniotic fluid cells obtained by routine amniocentesis. They were immortalized by the transfection of plasmid-carrying AV E1/pIX functions of human adenovirus serotype 5 (Ad5). CAP cells are well suitable for the production of therapeutic proteins with human identical post translational modifications and for the production of viral vectors. To summarize derivates of a CEVEC amniocyte production (CAP) cell (original cell line) are e.g. CAP-T cell, CAP-GT cell and CAP-Go cell. The CAP cell or said derivates may be used in the present invention, wherein these cell lines have been genetically modified to prevent LDLR expression on their cell surfaces.

The PER.C6 cell line is a commercial available manufacturing system that can be used to produce a variety of biopharmaceutical products, including vaccines, gene therapy products, antibodies and other therapeutic proteins. The PER.C6 cell line is derived from human embryonic retinal cells, originally from the retinal tissue of an 18 week old fetus aborted in 1985 and further developed and prepared as cell line by transfection with defined E1 region of the adenovirus type 5 followed by selection for transfectants with an immortal phenotype.

AGE1.HN is suitable for industrial, GMP-compliant virus-based vaccine production including RCA free adenovirus vectors, for recombinant proteins with specific complex glycans, other specific posttranslational modifications, and for proteins suffering from instability or susceptibility to proteolysis. The AGE1.HN cell line is derived from human neuronal cells and were immortalized with a combination of E1 genes from human adenovirus type 5.

The term "cell culture medium" as used herein includes liquids providing the chemical conditions which are required for HEK cell maintenance. Examples of chemical conditions which may support HEK cell expansion include but are not limited to solutions, buffers, serum, serum components, nutrients, vitamins, cytokines and other growth factors which are regularly provided in (or may be given manually to) the cell culture medium. Media suitable for use to cultivate HEK cells as known in the art include TexMACS (Miltenyi), CD FortiCHO™ Medium, FreeStyle™ 293, FreeStyle™ F-17, Expi293™ Expression Medium, Protein Expression Medium (PEM) (Thermo Fisher Scientific), HEK 293 Medium serum-free (Bio&Sell), Serum-free HEK Cell Culture Media (R&D Systems), HEK TF (Xell), DMEM (Biowest).

The term "introducing nucleic acids into a cell" means that nucleic acids such as DNA and/or RNA are introduced into a cell by methods well-known in the art for allowing the cell to uptake nucleic acids. Such methods are e.g. transfection, transduction, magnetofection and electroporation.

The term "transfection" means the introduction of nucleic acids with chemical compounds e.g. by using calcium phosphate, highly branched organic compounds, cationic polymers, lipofection or nanoparticles.

Pharmaceutical compositions based on the retroviral vector particle or virus-like particles thereof of the present invention may be formulated in any conventional manner using one or more physiologically acceptable carriers or excipients. Examples of generally used excipients include, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents.

Thus, the retroviral vector particle or virus-like particles thereof of the present invention may be formulated for administration by, for example, injection, inhalation or insulation (either through the mouth or the nose) or by oral, buccal, parenteral or rectal administration.

Such pharmaceutical compositions may be useful for transducing specifically target cells, which can include, inter alia, an immune cell, a cancerous cell or a stem cell, with the gene product of a desired protein that, if expressed in the targeted cell, leads to the prevention or the treatment of a particular medical condition.

EXAMPLES

Example 1: Generation of VSV-G Pseudotyped Lentiviral Vector

VSV-G pseudotyped lentiviral vector were generated by transient transfection of HEK 293T cells. HEK 293T cells were seeded on the day of transfection in 125 mL Shaker-flask (185 rpm) with 1.0E06 cells/mL in 25 mL serum-free cell culture medium and transfected with plasmids encoding VSV-G, gag/pol, rev and psi-positive transfer vector plasmids encoding for GFP (full plasmid system) or therapeutic relevant CD20-CAR. 24 h post transfection 10 mM sodium butyrate (Sigma-Aldrich, Cat: 3034 10-5004) was added. 48 h after transfection the lentiviral supernatant was harvested by centrifugation at 200×g to remove cell debris, aliquoted and stored at −80° C. for later use.

For the transfection of stable VSV-G expressing cell lines, HEK 293T cells were seeded in a 24-Well Plate one day before transfection in DMEM/10% FCS/0.8 µg/mL Puromycin (Biowest, Cat.No. 12362; Biochrom, Cat.No.S0415; Gibco, Cat.No. A11138-03). On the day of transfection only 3 plasmids of the 4 plasmid system were used: plasmids encoding for gag/pol, rev and a psi-positive transfer vector plasmid encoding for GFP. The following procedures are analogous to the transfection with the 4 plasmids.

Example 2: Titration of VSV-G Pseudotyped Lentiviral Vectors on HT1080

For the titration of lentiviral vectors, HT1080 cells cultivated in DMEM/10% FCS were seeded one day before transduction with 1.1E05 cells/well in 24-well-plates. On the day of transduction, the cell number was determined, the cells were washed with DMEM and transduced with particles encoding for GFP or CD20-CAR serially diluted in DMEM containing Polybrene® [8 µg/mL](Sigma Aldrich, Cat.No.H9268-5G). 72 h post transduction the transduction efficiency was determined by flow cytometry determining the ratio of GFP or CD20-CAR positive cells. The ratio of GFP positive cells, the dilution factor and the volume of lentiviral vector applied is used to calculate the lentiviral vector titer (i.e. transducing units per volume (TU/ml)).

Example 3: MACSQuant® Tyto®-Based Cell Sorting

To isolate LDLR negative or stably VSV-G expressing cells, multi-color based flow sorting was applied with the MACSQuant® Tyto® instrument that allows sorting within a single-use, disposable and fully closed cartridge. Cells were stained with a CD56 specific antibody (PE conjugated; Miltenyi Biotec, Cat: 130-098-137) and a CD71 specific antibody (VioBlue conjugated; Miltenyi Biotec, Cat: 130-101-631) to enable visualization of the cells to adjust flow sorting speed. In addition, antibodies specific for the antigen of interest were used (Human LDL R APC-conjugated Antibody, R&D-Systems, Cat: FAB2148A; Anti-VSV-G [8G5F11] Antibody, Kerafast, Cat: EB0010) to enable gating on the desired target cell population.

For actual sorting, cells suspended in MACSQuant® Tyto® running buffer at $4 \times 10^6$ cells/ml were transferred to a primed MACSQuant® Tyto® cartridge using a 10-mL syringe and a pre-separation filter (20 m) attached to the input chamber. Sorting was performed at 4° C. and the sort gate was set either on LDLR negative or on the high-expressing VSV-G positive cells. Afterwards, the sorted cells were suspended in DMEM/10% FCS and cultivated in a 24-well-plate.

Example 4: Autotransduction Rate on HEK 293T Cells

HEK 293T WT and HEK 293T LDLR neg pool cells were transfected with plasmids encoding for VSV-G, gag/pol, rev and psi-positive transfer vector plasmids encoding for GFP. As control, HEK 293T WT cells were incubated with autotransduction inhibitors Raltegravir [1 µM](Sigma-Aldrich, Cat: CDS023737) and 3'-Azido-3'-deoxythymidine (AZT) [10 µM](Sigma-Aldrich, Cat: A2169-25 mg). 24 h after transfection, 10 mM sodium butyrate was added. In 24 h intervals, the expression levels measured as mean fluorescence intensity (MFI) were determined by flow cytometry for 96 h. As the generated LV encodes for GFP, cells with high levels of autotransduction produce accumulating quantities of the transfer protein which is detectable as increasing MFI (FITC-Channel) over time as compared to cells with lower levels of autotransduction.

Example 5: LDLR Neg Cell Lines are Resistant to Autotransduction of Self-Produced LV Lentiviral vectors were generated by transfection of HEK 293T WT, HEK 239T LDLR neg pool and HEK 293T clone 1A1 and titrated on HT1080 as described in Example 1 and 2. The LV dose was adjusted to a multiplicity of infection (MOI) of 0.1 and 5.0E05 HEK 293T WT, HEK 293T LDLR neg pool or HEK 293T 1A1 were transduced. Three days post transduction, the transduction efficiency (%) was determined by flow cytometry. The relative transduction rates for lentiviral vectors generated on HEK 293T LDLR neg pool and HEK 293T 1A1 are calculated by normalization to transduction rates induced by LVs that were packaged by HEK 293T WT cells. By using the same LV dose, LDLR deficient cell lines are more resistant to autotransduction by self-produced LV as HEK 293T WT.

Example 6: Reduced Autotransduction Rates Determined by Measuring Copy Numbers of Integrated LV Proviral Genomes Per Transduced Cell by Quantitative Real-Time PCR HEK 293T WT, HEK 293T LDLR neg pool and HEK 293T LDLR neg clone 1A1 cells were transfected as described in example 1. Each culture were cultivated over 12 days to reduce false positive signals of remaining plasmids by dilution. To quantify the number of LV genomes integrated into the host cell genome by autotransduction, genomic DNA was isolated from each sample using the DNeasy Blood & Tissue Kit (50) (Qiagen, Cat: 69504).

For the quantification of the integrated provirus a primer and probe was designed specifically amplifying a 99 bp fragment between 5' LTR and internal promoter. A cellular reference gene was analogously quantified. A plasmid containing both the viral and cellular target sequences was constructed and served as standard. The ratio of viral to cellular copies was calculated. The transduction efficiency was also taken into account to determine the VCN for the transduced cells only.

Example 7: Single-Cell-Cloning and Clonal Selection

To obtain monoclonal subpopulations, the parental cell pool (either HEK 293T LDLR neg pool or HEK 293T 1A1 VSV-G pool) was diluted in DMEM/10% FCS to a statistical viable cell concentration of 0.5 cells/96 well in a total volume of 200 µl. Screening of LDLR negative single cell clones was based on the level of absent LDLR expression, low autotransduction rates and high LV productivity. Screening of stably expressing VSV-G single cell clones was based on high VSV-G expression levels and high LV productivity. Promising single cell clones were expanded to T-75 flasks and cryo-preserved stocks were generated.

Example 8: Generation of Stable VSV-G Expressing Cell Clones

HEK 293T WT, HEK 293T LDLR neg pool and HEK 293T LDLR neg clone 1A1 were seeded in 125 mL shaker flasks (185 rpm) at 1.0E06 cells/mL in 25 mL serum-free medium. 3 h post seeding the cell cultures were transfected with expression plasmids encoding VSV-G and an eukaryotic antibiotic resistance cassette allowing antibiotic-based selection (Puromycin, Gibco, Cat: A11138-03) of stably transfected cells. Two days post transfection selection was performed in serum-free medium containing 0.8 µg/mL Puromycin. The viability was determined in 48 h intervals. 9 days post transfection the suspension cultures were transferred into T75-flasks containing DMEM/10% FCS/0.8 µg/mL Puromycin to reach sufficient numbers of viable cells. Puromycin-resistant cells were only present for stably transfected HEK 293T LDLR neg cells (pool and clone 1A1). These were expanded to T175 flasks to obtain HEK 293T 1A1 VSV-G cells. Stable VSV-G expressing single cell clones were isolated with the MACSQuant® Tyto® gating on cells with high VSV-G expression levels, followed by single-cell-cloning as described above (see Example 3 and 7).

REFERENCES

Danit Finkelshtein, Ariel Werman, Daniela Novick, Sara Barak, Menachem Rubinstein (2015). LDL receptor and its family members serve as the cellular receptors for vesicular stomatitis virus. Proc Natl Acad Sci USA. 2013 Apr. 30; 110(18): 7306-7311.

Fouzia Amirache, Camille Lévy, Caroline Costa, Philippe-Emmanuel Mangeot, Bruce E. Torbett, Cathy X. Wang, Didier Negre, Francois-Loic Cosset and Els Verhoeyen (2014). Mystery solved: VSV-G-LVs do not allow efficient gene transfer into unstimulated T cells, B cells, and HSCs because they lack the LDL receptor. Blood 2014 123:1422-1424.

Jovan Nikolic, Laura Belot, Helene Raux, Pierre Legrand, Yves Gaudin & Aurélie A. Albertini (2018). Structural basis for the recognition of LDL-receptor family members by VSV glycoprotein. Nature Communications; Vol 9, 1029 (2018).

Alexander Otahal, Renate Fuchs, Faisal A. Al-Allaf, Dieter Blaas (2015). Release of Vesicular Stomatitis Virus Spike Protein G-Pseudotyped Lentivirus from the Host Cell Is Impaired upon Low-Density Lipoprotein Receptor Overexpression. J Virol. 2015 November; 89(22):11723-6.

Mireille Guyader, Etsuko Kiyokawa, Laurence Abrami, Priscilla Turelli, and Didier Trono (2002). Role for Human Immunodeficiency Virus Type 1 Membrane Cholesterol in Viral Internalization. J Virol. 2002 October; 76(20): 10356-10364.

Rodrigues, Ana & Alves, Paula & Coroadinha, Ana. (2011). Production of Retroviral and Lentiviral Gene Therapy Vectors: Challenges in the Manufacturing of Lipid Enveloped Virus. 10.5772/18615.

Otto-Wilhelm Merten; Matthias Schweizer; Parminder Chahal; Amine A Kamen (2014). Manufacturing of viral vectors for gene therapy: part I. Upstream processing. Pharmaceutical BioProcessing. 2(2):183-203, APR 2014.

The invention claimed is:

1. A method for producing vesicular stomatitis virus envelope protein (VSV-G) pseudotyped vectors that contain a Ψ-positive nucleic acid encoding one or more transgene products or virus-like particles thereof containing said transgene product(s),
    the method comprising:
    obtaining cells from a packaging cell line that has been stably adapted and/or selected to not express cell surface low density lipoprotein receptor (LDLR);
    causing the cells to express VSV-G, gag/pol, and optionally rev; and
    causing the cells to express said Ψ-positive nucleic acid or said transgene product(s), whereby the cells produce said pseudotyped vectors or virus-like particles; then
    harvesting from the cells said pseudotyped vectors or virus-like particles.

2. The method of claim 1, wherein the packaging cell line is a human cell line.

3. The method of claim 1, wherein the packaging cell line has been genetically engineered to prevent expression of LDLR on the cell surface.

4. The method of claim 3, wherein lentiviral mediated autotransduction by the packaging cell line is reduced by at least 50% as a result of being genetically engineered to prevent expression of LDLR on the cell surface.

5. The method of claim 3, wherein the packaging cell line has been adapted by knocking out or mutating a gene encoding LDLR to prevent expression of LDLR on the surface of cells from said line.

6. The method of claim 1, wherein the packaging cell line is selected from human embryonic kidney (HEK) cell line 293, HEK 293T, HEK EBNA, HEK 293F, HEK 293FT, and HEK 293-S.

7. The method of claim 1, wherein the packaging cell line has been genetically engineered to stably express VSV-G.

8. The method of claim 7, wherein the packaging cell line has been genetically engineered to stably express at least one additional gene selected from Gag/pol, rev, and said Ψ-positive nucleic acid that encodes said transgene product(s).

9. The method of claim 1, further comprising formulating the harvested vectors or virus-like particles as a pharmaceutical composition in a pharmaceutically acceptable carrier.

10. The method of claim 1, comprising co-transfecting the LDLR-negative packaging cells with a combination of vectors that include:
a Ψ-negative retroviral expression vector that encodes gag/pol,
a Ψ-negative retroviral expression vector that encodes VSV-G, and
said Ψ-positive nucleic acid.

11. The method of claim 1, comprising co-transfecting the LDLR-negative packaging cells with a combination of vectors that include:
a Ψ-negative retroviral expression vector that encodes gag/pol,
a Ψ-negative retroviral expression vector that encodes rev,
a Ψ-negative retroviral expression vector that encodes VSV-G, and
said Ψ-positive nucleic acid.

12. The method of claim 1, comprising co-transfecting the LDLR-negative packaging cells with a combination of vectors that include:
a Ψ-negative retroviral expression vector that encodes gag/pol and rev,
a Ψ-negative retroviral expression vector that encodes VSV-G, and
said Ψ-positive nucleic acid.

13. The method of claim 1, comprising co-transfecting the LDLR-negative packaging cells with a combination of vectors that include:
a Ψ-negative retroviral expression vector that encodes gag/pol,
a Ψ-negative retroviral expression vector that encodes rev, and
said Ψ-positive nucleic acid.

14. The method of claim 1, wherein the packaging cell line has been selected by sorting and recovering individual cells with relatively low levels of LDLR expression by flow cytometry, and establishing a cell line therefrom.

15. The method of claim 14, wherein the packaging cell line has been cloned and selected for a low level of LDLR expression.

16. A method for producing vesicular stomatitis virus G envelope protein (VSV-G) pseudotyped vectors that contain a Ψ-positive nucleic acid encoding one or more transgene products or virus-like particles thereof containing said transgene product(s), the method comprising:
adapting and/or selecting a population of packaging cells to not express low density lipoprotein receptor (LDLR);
causing the cells to express VSV-G, gag/pol, and optionally rev; and
causing the cells to express said Ψ-positive nucleic acid or said transgene product(s), whereby the cells produce said pseudotyped vectors or virus-like particles; then
harvesting from the cells said pseudotyped vectors or virus-like particles.

17. A combination configured for producing vesicular stomatitis virus G envelope protein (VSV-G) pseudotyped vectors containing a nucleic acid that encodes one or more transgene products, the combination comprising:
cells from a packaging cell line that has been stably adapted and/or selected to not express cell surface low density lipoprotein receptor (LDLR); along with
retrovirus expression vector(s) that encode VSV-G, gag/pol, and optionally rev.

18. The combination of claim 17, wherein the packaging cell line has been genetically engineered to prevent expression of LDLR on the surface of the cells.

19. The combination of claim 17, wherein the packaging cell line has been genetically engineered to stably express VSV-G, and
wherein the combination comprises retrovirus expression vector(s) that encode gag/pol, and rev.

20. The combination of claim 17, which further comprises an expression vector that contains the transgene.

21. The combination of claim 19, wherein the retrovirus expression vector(s) that encode gag/pol, and rev are Ψ-negative.

22. The combination of claim 20, wherein the expression vector that contains the transgene is Ψ-positive.

23. A combination configured for producing vesicular stomatitis virus G envelope protein (VSV-G) pseudotyped virus-like particles containing one or more transgene products, the combination comprising:
cells from a packaging cell line that has been stably adapted and/or selected to not express cell surface low density lipoprotein receptor (LDLR); along with
retrovirus expression vector(s) that encode VSV-G, gag/pol, and optionally rev.

24. A method of treating a subject in need thereof, comprising administering to the subject a pharmaceutical composition produced according to the method of claim 9.

* * * * *